United States Patent
Casella dos Santos

(10) Patent No.: US 9,569,594 B2
(45) Date of Patent: Feb. 14, 2017

(54) METHODS AND APPARATUS FOR GENERATING CLINICAL REPORTS

(75) Inventor: Mariana Casella dos Santos, Ghent (BE)

(73) Assignee: Nuance Communications, Inc., Burlington, MA (US)

( * ) Notice: Subject to any disclaimer, the term of this patent is extended or adjusted under 35 U.S.C. 154(b) by 705 days.

(21) Appl. No.: 13/415,606

(22) Filed: Mar. 8, 2012

(65) Prior Publication Data

US 2013/0238330 A1 Sep. 12, 2013

(51) Int. Cl.
*G06F 19/00* (2011.01)
*G10L 15/183* (2013.01)

(52) U.S. Cl.
CPC ......... *G06F 19/3487* (2013.01); *G10L 15/183* (2013.01); *G06F 19/322* (2013.01)

(58) Field of Classification Search
CPC .. G06F 19/3487; G06F 17/278; G06F 19/322; G10L 15/183; G10L 15/26
See application file for complete search history.

(56) References Cited

U.S. PATENT DOCUMENTS

| | | | |
|---|---|---|---|
| 5,809,476 A | 9/1998 | Ryan | |
| 6,266,635 B1 * | 7/2001 | Sneh | 704/235 |
| 6,401,063 B1 * | 6/2002 | Hebert et al. | 704/234 |
| 6,589,169 B1 * | 7/2003 | Surwit et al. | 600/300 |
| 6,801,916 B2 * | 10/2004 | Roberge et al. | |
| 6,915,254 B1 | 7/2005 | Heinze et al. | |
| 7,493,253 B1 | 2/2009 | Ceusters et al. | |
| 7,496,500 B2 * | 2/2009 | Reed | G06Q 10/107 704/270 |
| 2002/0082825 A1 * | 6/2002 | Rowlandson et al. | 704/9 |
| 2003/0105638 A1 | 6/2003 | Taira | |
| 2003/0125940 A1 * | 7/2003 | Basson et al. | 704/231 |
| 2004/0162728 A1 * | 8/2004 | Thomson et al. | 704/255 |
| 2004/0186712 A1 * | 9/2004 | Coles et al. | 704/235 |
| 2005/0055215 A1 * | 3/2005 | Klotz | 704/275 |
| 2006/0041428 A1 | 2/2006 | Fritsch et al. | |
| 2007/0169021 A1 | 7/2007 | Huynh et al. | |
| 2007/0233488 A1 | 10/2007 | Carus et al. | |

(Continued)

FOREIGN PATENT DOCUMENTS

EP 1 769 771 A1 4/2007
WO WO 00/08585 A2 2/2000

OTHER PUBLICATIONS

Invitation to Pay Additional Fees for PCT/US2012/072041 mailed Jun. 6, 2013.

(Continued)

*Primary Examiner* — Angela A Armstrong
(74) *Attorney, Agent, or Firm* — Wolf, Greenfield & Sacks, P.C.

(57) ABSTRACT

Techniques for documenting a clinical procedure involve transcribing audio data comprising audio of one or more clinical personnel speaking while performing the clinical procedure. Examples of applicable clinical procedures include sterile procedures such as surgical procedures, as well as non-sterile procedures such as those conventionally involving a core code reporter. The transcribed audio data may be analyzed to identify relevant information for documenting the clinical procedure, and a text report including the relevant information documenting the clinical procedure may be automatically generated.

87 Claims, 6 Drawing Sheets

(56) References Cited

U.S. PATENT DOCUMENTS

2009/0187407 A1* 7/2009 Soble et al. .................. 704/260
2010/0088095 A1 4/2010 John
2012/0215559 A1 8/2012 Flanagan et al.

OTHER PUBLICATIONS

International Search Report and Written Opinion for PCT/US2012/072041 mailed Aug. 2, 2013.
Alapetite et al., Introducing vocal modality into electronic anaesthesia record systems: possible effects on work practices in the operating room. EACE '05 Proceedings of the 2005 Annual Conference on European Association of Cognitive Ergonomics. Jan. 1, 2005:197-204.
Grasso et al., Automated Speech Recognition in Medical Applications. M.D. Computing. Jan. 11, 1995:12(1):16-23.
Jungk et al., A Case Study in Designing Speech Interaction with a Patient Monitor. J Clinical Monitoring and Computing. May 1, 2000;16(4):295-307.
Meng et al., Generating Models of Surgical Procedures using UMLS Concepts and Multiple Sequence Alignment. AMIA Annu Symp Proc. Jan. 1, 2005:520-24.
Zafar et al., Continuous Speech Recognition for Clinicians. J Am Med Infor Assoc. Jan. 1, 1999;6(3):195-204.
PCT/US2012/072041, Jun. 6, 2013, Invitation to Pay Additional Fees.
PCT/US2012/072041, Aug. 2, 2013, International Search Report and Written Opinion.
U.S. Appl. No. 13/415,545, filed Mar. 8, 2012, Casella dos Santos.
Cimiano et al., "Learning concept hierarchies from text with a guided hierarchical clustering algorithm," In C. Biemann and G. Paas (eds.), Proceedings of the ICML 2005 Workshop on Learning and Extending Lexical Ontologies with Machine Learning Methods, Bonn, Germany, (2005).
Fan et al., "Prismatic: Inducing Knowledge from a Large Scale Lexicalized Relation Resource," Proceedings of the NAACL HLT 2010 First International Workshop on Formalisms and Methodology for Learning by Reading, pp. 122-127, Los Angeles, California, Jun. 2010.
Florian et al., "A Statistical Model for Multilingual Entity Detection and Tracking," Proceedings of the Human Language Technologies Conference 2004 (HLT-NAACL'04), (2004).
Gomez-Perez et al., "An overview of methods and tools for ontology learning from texts," Knowledge Engineering Review 19:3 p. 187-212, 2004.
Harris, "Building a Large-scale Commercial NLG System for an EMR". Proceedings of the Fifth International Natural Language Generation Conference. pp. 157-160, (2008).
Klann et al., "An intelligent listening framework for capturing encounter notes from a doctor-patient dialog," BMC Medical Informatics and Decision Making 2009, 9(Suppl I):S3, Published Nov. 3, 2009.
MIT Computer Science and Artificial Intelligence Laboratory (CSAIL) Clinical Decision Making Group, "Fair Witness: —Capturing Patient-Provider Encounter through Text, Speech, and Dialogue Processing," Last updated on Apr. 9, 2010, Last accessed on May 26, 2011 from http://groups.csail.mit.edu/medg/projects/fw/ 3 pages.
Welty et al., "Large Scale Relation Detection," Proceedings of the NAACL HLT 2010 First International Workshop on Formalisms and Methodology for Learning by Reading, pp. 24-33, Los Angeles, California, Jun. 2010.

* cited by examiner

102 — PREOPERATIVE DIAGNOSIS: perforated appendicitis.

POSTOPERATIVE DIAGNOSIS: perforated appendicitis.

104 — NAME OF PROCEDURE:
1. Appendectomy. 2. Lysis of adhesions.

106 — SURGEON: Michael Jordan, MD

ASSISTANT: Venus Williams, PA-C.

ANESTHESIOLOGIST: Peter Sampras, MD

108 — ANESTHESIA:
General endotracheal with additional 12 mL of 0.25% Marcaine with epinephrine injected at the incision site prior to incision.

110 — INDICATION FOR OPERATION:
A 55-year-old female with a 2-week history of right lower quadrant pain. The patient presented to Utopia Hospital emergency department today. The patient had a tender mass in her right lower quadrant. Her white blood count was elevated to approximately 16. CT scan was obtained which was consistent with a contained abscess in the right lower quadrant, most likely from perforated appendicitis. The patient and her close family friend were fully counseled on the risks, benefits, and alternatives of open appendectomy with abdominal exploration. Risks include, but are not limited to, infection, bleeding, damage to surrounding structures, postoperative abscess, complications due the patient's medications for her rheumatoid arthritis or other medical problems, need for additional procedures for another postoperative abscess, use of drains, doing additional procedures as indicated with intraoperative findings, as well as cardiopulmonary risk of anesthesia. They understood all and both strongly concurred with the plan.

OPERATIVE FINDINGS:
As indicated by the CT, there was an abscess cavity in the right lower quadrant surrounded by the cecum, omentum, and distal small intestine. There was a small stump consistent with the appendix that essentially had an obliterated lumen; it was too short to attempt any type of stapling, and the tissue was too friable to attempt to tie anything off, although this was attempted. The rest of the appendix could not be found. There was an omental adhesion in the area that was causing a partial closed loop small-bowel obstruction with ischemic bowel in the right lower quadrant; however, once this was released, the bowel returned to a normal color. The proximal bowel was normal in appearance and caliber. All the omental adhesions were taken down to include some prior pelvic omental adhesions, probably secondary to the patient's exploratory laparotomy many years ago.

114

GRAFTS: None.

116

SPECIMENS: None.

118

DRAINS:
A 10-French JP drain, Foley catheter.

120

ESTIMATED BLOOD LOSS: 100 mL.

122

DEEP VEIN THROMBOSIS PROPHYLAXIS: SCDs. Note, we will plan to place the patient on Lovenox as soon as a stable hematocrit is seen.

124

ANTIBIOTICS:
Invanz 1 g IV preoperatively.

126

COMPLICATIONS: None.

128

SPONGE, NEEDLE, AND INSTRUMENT COUNT:
Correct at the end of procedure.

DESCRIPTION: The patient was in the supine position. SCDs were in place. The patient underwent general endotracheal anesthesia. A Foley catheter was placed without incident. The abdomen was sterilely prepped and draped. A final time-out was called. A midline incision was made from 2 fingerbreadths above the umbilicus to 4 fingerbreadths below. Care was taken to slowly enter the peritoneal cavity. The omental adhesions were sharply taken down from the abdominal wall. Initially the right lower quadrant abscess cavity was located and entered. Suctioning was immediately done with suctioning of perhaps 30-50 mL of purulent fluid. Irrigation was also immediately done. The irrigant came back clear. Further dissection was then done to attempt to locate the appendix. The cecum was identified. The terminal ileum was identified. There did appear to be some dusky bowel. The bowel was run proximally a distance of approximately 12 to 24 inches from the cecum. An omental adhesion was found that was causing closed-loop obstruction. This was lysed. The bowel was observed throughout the rest of the case. It was no longer ischemic. During this time, a small serosal small tear was made in part of the terminal ileum that was within the surrounding wall of the abscess. The serosa was intact; however, three 3-0 PDS were used to approximate and cover the serosa defect. The omental adhesions in the pelvis were then taken down, as there was a potential with that for causing an internal hernia, given these adhesions. The omentum was then placed in its normal position overlying the small intestine. A JP drain was placed in the abscess cavity via a separate right lower quadrant stab incision. As noted during the case, the appendix was searched for. The distal portion could not be found. More than likely, this simply was hydrolyzed and obliterated within the abscess cavity. Regardless, it was deemed that further dissection would not be beneficial to the patient, especially given her other comorbidities; therefore, the abdomen was then closed under direct vision with #1 looped PDS. There was no impingement upon the bowel. The skin was then closed over the top of a Penrose drain, given the risk of wound infection. Also of note, the patient had very unhealthy subcutaneous fat and weak fascia consistent with her prednisone use. Given the operative findings, it was decided the patient would need a central line. This is going to be placed while the patient is still under general anesthesia. In addition, Dr. Sampras, the anesthesiologist, will attempt to place a nerve block to assist with postoperative pain. We do anticipate some issues with postoperative pain control, given the patient's chronic pain state secondary to rheumatoid arthritis. The patient was then, after all procedures were done, awakened, extubated, and taken to the recovery room stable condition. The patient will be observed in the intensive care unit at least overnight. I did relate the results of the operative procedure and the plan with the patient's close family friend. He understands and concurs with the plan.

FIG. 1C

METHODS AND APPARATUS FOR GENERATING CLINICAL REPORTS

BACKGROUND OF INVENTION

1. Field of Invention

The techniques described herein are directed generally to the field of clinical documentation, and more particularly to techniques for facilitating the creation of clinical procedure reports.

2. Description of the Related Art

Clinical documentation is an important process in the healthcare industry. Most healthcare institutions maintain a longitudinal medical record (e.g., spanning multiple observations or treatments over time) for each of their patients, documenting, for example, the patient's history, encounters with clinical staff within the institution, treatment received, and/or plans for future treatment. Such documentation facilitates maintaining continuity of care for the patient across multiple encounters with various clinicians over time. In addition, when an institution's medical records for large numbers of patients are considered in the aggregate, the information contained therein can be useful for educating clinicians as to treatment efficacy and best practices, for internal auditing within the institution, for quality assurance, etc.

One exemplary type of clinical documentation that may be included in a patient's medical record is a clinical procedure report documenting a clinical procedure performed on the patient. For example, one type of clinical procedure is a surgical procedure. Typically, a surgeon who performs a procedure on a patient later creates a report (often referred to as an "operative report") that documents the procedure in textual form. The operative report may relate information such as the reason(s) for the procedure, the preoperative and postoperative diagnoses, actions that were taken and events (including complications) that occurred during the procedure, observations that were made during the procedure, indications for future treatment, etc. To save time, surgeons conventionally dictate these operative reports by speaking into a recording device, and the speech is then transcribed (e.g., by a medical transcriptionist) to create the text report.

SUMMARY OF INVENTION

One type of embodiment is directed to a method comprising transcribing audio data comprising audio of one or more clinical personnel speaking while performing a surgical procedure; analyzing the transcribed audio data, using at least one processor, to identify relevant information for documenting the surgical procedure; and automatically generating a text report including the relevant information documenting the surgical procedure.

Another type of embodiment is directed to apparatus comprising at least one processor; and at least one memory storing processor-executable instructions that, when executed by the at least one processor, perform a method comprising transcribing audio data comprising audio of one or more clinical personnel speaking while performing a surgical procedure, analyzing the transcribed audio data to identify relevant information for documenting the surgical procedure, and automatically generating a text report including the relevant information documenting the surgical procedure.

Another type of embodiment is directed to at least one computer-readable storage medium encoded with computer-executable instructions that, when executed, perform a method comprising transcribing audio data comprising audio of one or more clinical personnel speaking while performing a surgical procedure; analyzing the transcribed audio data to identify relevant information for documenting the surgical procedure; and automatically generating a text report including the relevant information documenting the surgical procedure.

Another type of embodiment is directed to a method comprising transcribing audio data comprising audio of one or more clinical personnel speaking while performing a sterile procedure; analyzing the transcribed audio data, using at least one processor, to identify relevant information for documenting the sterile procedure; and automatically generating a text report including the relevant information documenting the sterile procedure.

Another type of embodiment is directed to apparatus comprising at least one processor; and at least one memory storing processor-executable instructions that, when executed by the at least one processor, perform a method comprising transcribing audio data comprising audio of one or more clinical personnel speaking while performing a sterile procedure, analyzing the transcribed audio data to identify relevant information for documenting the sterile procedure, and automatically generating a text report including the relevant information documenting the sterile procedure.

Another type of embodiment is directed to at least one computer-readable storage medium encoded with computer-executable instructions that, when executed, perform a method comprising transcribing audio data comprising audio of one or more clinical personnel speaking while performing a sterile procedure; analyzing the transcribed audio data to identify relevant information for documenting the sterile procedure; and automatically generating a text report including the relevant information documenting the sterile procedure.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 1A, 1B and 1C illustrate an example of an operative report that may be generated in accordance with some embodiments of the present invention;

DETAILED DESCRIPTION

Figure 2:
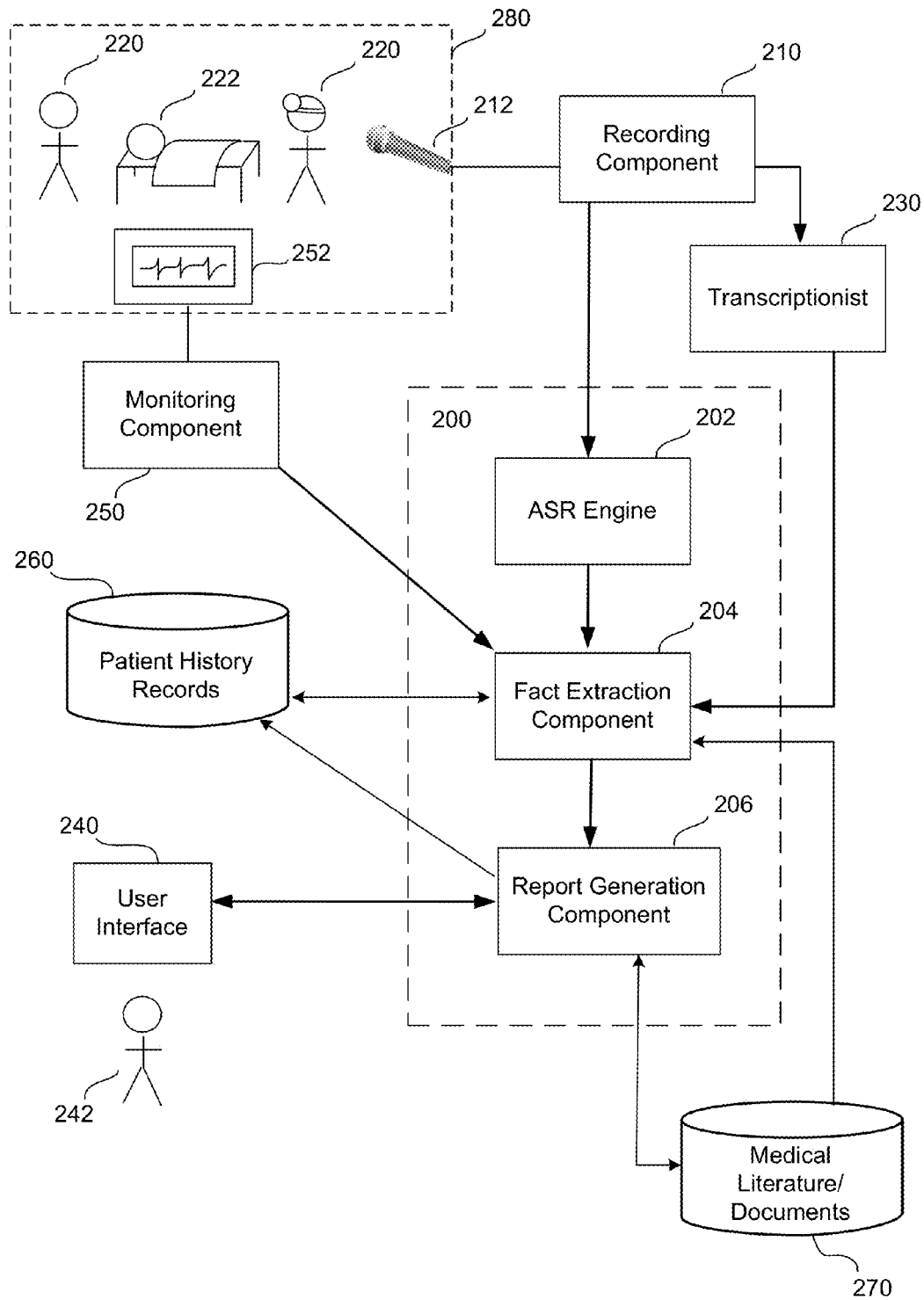
FIG. 2 is a block diagram illustrating an exemplary operating environment for a system in accordance with some embodiments of the present invention.

Shown in FIG. 1 is an example of an operative report. Exemplary operative report 100 was created to document an appendectomy procedure, which is a particular type of surgical procedure. This is just a single example provided for illustrative purposes; it should be appreciated that operative reports may be created to document any suitable procedure(s), may take any suitable form and may include any suitable content, as aspects of the invention are not limited to any particular operative report or type of operative report.

Typically, an operative report is divided into a number of sections delineated by section headings, as illustrated in FIG. 1. The inclusion of some of the sections may be required by one or more applicable standards that specify certain items that must be documented in an operative report for a particular type of procedure, for a particular institution (e.g., a hospital) in which the procedure is performed, and/or for operative reports in general. Other sections of the operative report in some cases may be included by preference of the surgeon or other clinician who creates the report, or may be pertinent for a particular patient, a particular procedure performed, etc. One widely adopted set of standards for operative report content in the United States is promulgated by the Joint Commission on Accreditation of Healthcare Organizations (JCAHO). Another notable set of standards is promulgated by Health Level Seven (HL7). Other standards are available as well, including standards created and/or applied at a more local or institutional level. Any of these standards may be revised at various points in time, and new standards may be developed as the healthcare industry evolves. It should be appreciated that techniques disclosed herein are not limited to any particular standard for report content, although some embodiments may allow for conformance to particular standards.

Example operative report 100 begins in FIG. 1A with sections 102 setting forth the patient's diagnoses related to the surgical procedure. The section heading "PREOPERATIVE DIAGNOSIS" introduces the statement of the diagnosis that was determined for the patient before the surgical procedure was performed—in this case, "perforated appendicitis." The section heading "POSTOPERATIVE DIAGNOSIS" introduces the statement of the diagnosis given to the patient after the procedure was completed. In this case, the preoperative and postoperative diagnoses are the same; however, in some cases the diagnosis or set of diagnoses may change as a result of the procedure. For example, clinical observations during the procedure may give rise to a change in diagnosis, the addition of a new diagnosis, and/or elimination of a previous diagnosis.

Example operative report 100 continues with section 104 documenting the name(s) of the procedure(s) performed during the operation. In this case, two procedures were performed—an appendectomy, and lysis of adhesions. Section 106 then states the name(s) of one or more of the clinical personnel involved in performing the surgical procedure. The surgeon is the primary physician in charge of performing the surgical procedure, and is often the person who dictates or otherwise completes the operative report. The assistant may be another physician or a non-physician clinician (e.g., a medical student or a physician assistant) who assists the surgeon in performing the surgical procedure, but is not in charge of the surgical procedure. In this case, the post-nominal initials "PA-C" indicate that Venus Williams is a certified physician assistant, who is licensed to practice medicine under the supervision of a physician. The anesthesiologist is the physician responsible for administering and/or monitoring anesthesia to sedate the patient during the surgical procedure. In some cases, there may be more than one surgeon, assistant and/or anesthesiologist involved in the surgical procedure who may be listed in the operative report. Not all operative reports include a listing of surgeon, assistant and anesthesiologist; some procedures may not involve one or more of these personnel, and some reports may not list one or more of these personnel even though they were involved in the procedure. In addition, other clinical personnel may also be involved in performing the surgical procedure (e.g., nurses, residents, consulting physicians and/or other clinical staff), and any of these personnel may or may not be listed in the operative report. In some cases, the clinical personnel to be listed in the operative report may be determined by an applicable standard for report content, such as a national or institutional standard, and/or by the preferences of the clinician creating and/or approving the report. Some operative reports may also list the name or other identification of the patient; although this may not be necessary, for example, if the patient's identity is clear from the inclusion of the operative report in the patient's medical file or "chart," or from metadata associated with the report in electronic form. Aspects of the invention described herein are not limited to the listing of any particular personnel in an operative report, although some embodiments may allow for such information to be included.

Section 108 of example operative report 100 documents the type and/or dosage of anesthesia delivered to the patient during the surgical procedure. Section 110, with heading "INDICATION FOR OPERATION," then relates the preoperative events and/or observations that led to the surgical procedure being selected for the patient. Report content standards often also suggest or require documentation to establish the patient's informed consent to the procedure. Exemplary section 110 therefore relates how the patient was counseled on the risks, benefits and alternatives of the procedure, how the patient understood the counseling and how he or she agreed to have the procedure performed. In some other cases, such informed consent documentation may be included as a separate section of the operative report, rather than together with the patient's presenting symptoms, or may not be included at all. It should be appreciated that aspects of the invention are not limited to the inclusion of any particular information in an operative report, although some embodiments provide techniques for the inclusion of required (e.g., by an institutional or other standard) or otherwise appropriate content, e.g., for quality assurance purposes.

Example operative report 100 continues in FIG. 1B with section 112, with heading "OPERATIVE FINDINGS." This section relates observations that were made during the surgical procedure, some of which may be relevant to the patient's postoperative diagnosis, to decisions that were made during performance of the procedure, and/or to indications for the patient's further treatment. Example operative report 100 then continues with a number of sections, some of which may be required by an applicable report content standard, some of which may be included routinely by the clinician creating the report, and/or some of which may be appropriate for the particular procedure being performed. Section 114 documents any tissue that was grafted into the patient, while section 116 documents any tissue specimens that were removed from the patient. Section 118 documents a drain that was placed in the patient to remove fluid from the patient's abscess. Section 120 documents the estimated amount of blood that the patient lost during the procedure. Section 122 documents any measures that were taken to prevent deep vein thrombosis, which can result from reduced and/or altered blood flow caused by surgery, by prolonged bed rest after surgery, etc. Section 124 documents any antibiotics that were administered to the patient, e.g., to prevent infection of the surgical wounds. Section 126 documents any complications that occurred during the procedure. Section 128 documents the sponge, needle and instrument count, e.g., to confirm that no such items were accidentally left inside the patient's body. It should be appreciated that aspects of the present invention are not limited to the inclusion of any of the foregoing sections in an operative report; any, all or none of these sections may be included, and other appropriate sections not mentioned above may be included, as appropriate for a particular procedure, institution or clinician, and/or as required by any applicable report content standard.

Example operative report 100 concludes in FIG. 1C with a section 130 describing the surgical procedure itself. This may be the main narrative of the operative report supplied, e.g., by the surgeon or other primary physician responsible for the operation. Section 130 describes in detail the actions that were performed during the procedure, the observations that were made, and events that occurred during the procedure. This section may also include some of the physician's thoughts about the patient's prognosis and recommendations for further treatment, although such information may alternatively be documented in a separate section or may not be included in the report. Typically, the section of the operative report narrating the surgical procedure is the section most left to the discretion of the physician and/or to the particularities of the patient and/or of the procedure performed, although applicable report content standards may also specify certain types of information that should be included in the narrative. A physician typically will try to narrate all information that may be useful to know for future treatment or advising of the patient, as well as information that may be useful as evidence that proper procedure was followed and that best efforts were made with regard to the patient's ongoing health. It should be appreciated, however, that aspects of the invention are not limited to any particular content in the description of a surgical procedure, and that techniques described herein may be used to produce narrations of any suitable content.

During a surgical procedure, the clinical personnel involved often orally communicate a great deal of information to each other, e.g., to help them perform the procedure correctly and efficiently together as a team. For instance, the surgeon often narrates his or her actions out loud as he or she performs them, which may serve to alert the other personnel to what is currently happening in the procedure, allowing them to effectively prepare and assist. For example, the surgeon may say aloud, "I'm now lysing the omental adhesion," as he or she begins to perform the associated action. Other personnel may also narrate out loud as they perform their own actions. Clinical personnel may also narrate their observations of events, complications and/or conditions during the procedure, such as, "Blood pressure is dropping," or "I don't see the appendix," etc. Also, clinical personnel often mention out loud the instruments used during the surgical procedure. In one example, the surgeon may ask for the "scalpel," and a nurse may reply, "scalpel," as he or she passes the scalpel to the surgeon. In addition to such interactions during the procedure, nurses or other clinical personnel often also make an oral inventory of the instruments and/or other materials present in the operating room before and/or after the surgical procedure is performed.

The inventor has recognized that much of the information typically included in an operative report may be gleaned from oral communication that occurs during the surgical procedure that the report is created to document. Yet, conventionally, none of that oral communication is put to use toward documenting the procedure. Instead, physicians conventionally must wait until sometime after the procedure is completed, and then must attempt to recall everything that happened and was observed, while dictating or otherwise creating the operative report from scratch. The inventor has appreciated that this can be a tedious procedure for physicians (for whom time can be very valuable), and also can give rise to errors and/or omissions in the documentation due to the limitations of human memory. The inventor has recognized and appreciated that by capturing and utilizing the oral communication that already takes place during surgical procedures, operative reports may be automatically generated in a way that may both save clinicians valuable time and effort, and also increase the quality of documentation of surgical procedures, which may provide numerous benefits. For example, more detailed and more accurate clinical documentation can enhance the efficiency of billing, promote quality assurance initiatives, decrease liability, increase available data for medical research, training and decision support, etc.

Accordingly, some embodiments described herein relate to techniques for automatically generating a report (e.g., a text report) for documenting a surgical procedure, using audio of one or more clinical personnel speaking while performing the surgical procedure. In some embodiments, speech recognition may be performed on the audio recorded during the surgical procedure, and the recognized speech may then be analyzed to identify and extract relevant information to include in the operative report.

As discussed further below, techniques described herein may also be applied in contexts other than those limited to surgery. For example, some embodiments relate more generally to documenting sterile procedures (which may be surgical or non-surgical), which may require a sterile environment and/or may especially require the clinician's hands and/or gloves to be sterile while performing the procedure. For such procedures, a clinician may not be able to carry a speech recording device by hand, and/or may not be able to access a computer terminal or other typing or writing tool to document the procedure in real time. One example of such a sterile procedure is a percutaneous endoscopy procedure, in which an endoscope is used to internally examine a body cavity of the patient. Such percutaneous endoscopies may involve one or more incisions to insert one or more scopes into a normally closed body cavity. Other examples of sterile procedures include any of various procedures that may be performed on a patient who is kept in isolation due to immunodeficiency or contagious disease. Clinicians providing care to such patients may be required to sterilize their hands upon entering and/or exiting the isolation room.

Other embodiments relate to documenting non-sterile procedures that involve real-time narration and/or documentation of the procedure while requiring the clinician to have his or her hands unencumbered to perform the procedure. One example of this type of procedure is in the field of pathology, in which a pathologist may narrate his or her findings while dissecting or otherwise analyzing a body, organ, tissue sample or the like. Another example is an endoscopy that is performed non-surgically using a natural opening of the human body (e.g., the mouth or nose), to examine a body tract of the patient. Yet another example is an attempt to resuscitate a patient during a type of emergency involving detailed documentation by a core code recorder.

The aspects of the present invention described herein can be implemented in any of numerous ways, and are not limited to any particular implementation techniques. Thus, while examples of specific implementation techniques are described below, it should be appreciated that the examples are provided merely for purposes of illustration, and that other implementations are possible.

One illustrative application for the techniques described herein is for use in a system for facilitating the creation of clinical procedure reports. An exemplary operating environment for such a system is illustrated in FIG. 2. The exemplary operating environment includes a procedure documenting system 200, which may be implemented in any suitable form, as aspects of the present invention are not limited in this respect. For example, system 200 may be implemented as a single stand-alone machine, or may be implemented by multiple distributed machines that share processing tasks in any suitable manner. System 200 may be implemented as one or more computers; an example of a suitable computer is described below. In some embodiments, system 200 may include one or more tangible, non-transitory computer-readable storage devices storing processor-executable instructions, and one or more processors that execute the processor-executable instructions to perform the functions described herein. The storage devices may be implemented as computer-readable storage media encoded with the processor-executable instructions; examples of suitable computer-readable storage media are discussed below.

As depicted, system 200 includes an automatic speech recognition (ASR) engine 202, a fact extraction component 204, and a report generation component 206. Each of these processing components of system 200 may be implemented in software, hardware, or a combination of software and hardware. Components implemented in software may comprise sets of processor-executable instructions that may be executed by the one or more processors of system 200 to perform the functionality described herein. Each of ASR engine 202, fact extraction component 204 and report generation component 206 may be implemented as a separate component of system 200 (e.g., implemented by hardware and/or software code that is independent and performs dedicated functions of the component), or any combination of these components may be integrated into a single component or a set of distributed components (e.g., hardware and/or software code that performs two or more of the functions described herein may be integrated, the performance of shared code may be distributed among two or more hardware modules, etc.). In addition, any one of ASR engine 202, fact extraction component 204 and report generation component 206 may be implemented as a set of multiple software and/or hardware components. Although the example operating environment of FIG. 2 depicts ASR engine 202, fact extraction component 204 and report generation component 206 implemented together on system 200, this is only an example; in other examples, any or all of the components may be implemented on one or more separate machines, or parts of any or all of the components may be implemented across multiple machines in a distributed fashion and/or in various combinations. It should be understood that any such component depicted in FIG. 2 is not limited to any particular software and/or hardware implementation and/or configuration.

ASR component 202 may receive speech data via any suitable communication medium or media (e.g., local and/or network connection(s) that may include wired and/or wireless connection(s)) from recording component 210. Recording component 210 may be implemented in any suitable way to record audio data from one or more microphones 212 or other audio detecting and/or receiving devices. References to microphone(s) as used herein should be interpreted to include any suitable device(s) capable of receiving and transducing audio signals into a form that can be stored by recording component 210 and/or processed by ASR engine 202, as aspects of the invention are not limited to any particular type of audio receiving device. Recording component 210 may be implemented in hardware, software, or a combination of hardware and software, and may include dedicated recording circuitry and/or one or more processors programmed to record (e.g., store) audio received from microphone(s) 212 in a form usable by ASR engine 202 and/or by transcriptionist 230. Alternatively, audio data may be received by ASR engine 202 directly from microphone(s) 212 for processing. The audio data may be represented in any suitable form, such as an analog or digital waveform or a sequence of acoustic feature vectors, and may be encoded in any suitable data format, as aspects of the invention are not limited in this respect.

In some embodiments, recording component 210 may have a local connection to microphone(s) 212, such as via one or more wires or cables capable of transmitting an audio signal. Alternatively, recording component 210 may have a wireless and/or network connection to microphone(s) 212, or may have wired connection(s) to some microphone(s) 212 and non-wired connection(s) to other microphone(s) 212. Microphone(s) 212 may be located in a procedure room 280, and recording component 210 may be locally connected and located nearby, e.g., in a machine housing within procedure room 280, within a wall of procedure room 280, or in an adjacent room. Alternatively, in some embodiments recording component 210 may be integrated with ASR engine 202, on system 200 or in a separate machine or device, and recording component 210 may receive transduced audio from microphone(s) 212 remotely via any suitable network connection or other communication medium or media. In some other embodiments, ASR engine 202 may be integrated locally with recording component 210 within or near procedure room 280, or system 200 with all its components may even be local to procedure room 280. It should be appreciated that any component or components of the operating environment illustrated in FIG. 2 may be implemented locally or remotely in any suitable combination, as aspects of the invention are not limited in this respect.

As illustrated in FIG. 2, one or more clinical personnel 220 may be present in procedure room 280, performing a clinical procedure on patient 222. When the procedure is a surgical procedure (one type of sterile procedure), procedure room 280 may be an operating room (OR), and clinical personnel 220 may include one or more surgeons, one or more anesthesiologists, one or more other physicians, one or more assistants, one or more residents, one or more nurses, and/or any other appropriate personnel participating in performing and/or supporting the surgical procedure. When the procedure is, for example, a pathology procedure (one type of non-sterile clinical procedure), procedure room 280 may be a pathology laboratory, and clinical personnel 220 may include one or more pathologists, and/or any appropriate assistants or other personnel participating in performing and/or supporting the pathology procedure. In this case, the depiction of "patient" 222 may represent a cadaver for autopsy, or one or more organs or tissue samples taken from a patient for pathology analysis. In general, when the procedure is a non-sterile procedure, procedure room 280 may be any suitable location; for example an ambulance, an emergency room or other hospital room in which resuscitation is performed on a patient 222 experiencing cardiac arrest.

In some embodiments, microphone(s) 212 may be installed within procedure room 280 in a relatively permanent manner, such that they remain in fixed positions during, between and across multiple successive procedures performed in procedure room 280. For example, in some embodiments microphone(s) 212 may be affixed to the ceiling and/or walls of procedure room 280, or may be attached to light fixtures and/or other equipment or machinery in fixed locations within procedure room 280. In some embodiments, multiple microphones 212 may be installed within procedure room 280 such that audio can be collected from sources in all parts of the room, or in a suitable portion of the room to collect useful audio for documenting the procedure. Alternatively or additionally, in some embodiments microphone(s) 212 may be installed in particular locations and/or orientations within procedure room 280 based on the normal positions of particular clinical personnel during procedures. For example, one or more microphones 212 may be installed near the operating table facing the position in which the surgeon normally stands, and/or one or more microphones 212 may be installed near the anesthesia machines facing the anesthesiologist. In other embodiments, microphone(s) 212 may be worn by individual clinical personnel in such a way that their speech is captured by their own microphone(s) in a consistent fashion as they move around procedure room 280. As used herein, the reference to microphones being "worn" by clinical personnel refers to attaching the microphones to a portion of the body, to clothing, and/or to any other suitable accessory carried on the body, in a way that does not involve carrying the microphone in the hand. However, in some embodiments, one or more microphones may alternatively or additionally be carried by hand. Such microphones worn and/or carried by clinical personnel may be used instead of microphones installed in procedure room 280 itself, or in addition to other microphones installed in procedure room 280 in a fixed manner.

As clinical personnel 220 are performing the clinical procedure on patient 222, they may communicate orally to each other through speech. As discussed above, this oral communication may include narration of actions being performed and/or drugs or other substances being administered in connection with the procedure, acknowledgment of events occurring during the procedure, observations of complications occurring and/or conditions presenting in the patient, inventory of instruments and/or other materials present and/or used in the procedure, and/or other information relevant for documenting the clinical procedure. In some embodiments, some or all of this speech may be captured as one or more audio signals and stored by recording component 210 as audio data. As discussed below, such audio data may then be transcribed manually by a human transcriptionist 230 and/or automatically by ASR engine 202. Alternatively, as discussed above, audio data from microphone(s) 212 may be processed directly by ASR engine 202, without being handled by a separate recording component 210. In yet other embodiments, oral communication occurring in procedure room 280 may be transcribed in real time by a human such as a stenographer, without requiring microphone(s) 212, recording component 210 or ASR engine 202. Thus, it should be appreciated that in some embodiments, audio data representing oral communication may be transcribed in any suitable way, as some embodiments are not limited in this respect.

In some embodiments, the audio may be stored (e.g., by recording component 210 in some embodiments) and/or processed as a single stream or signal, without consideration of which individual was speaking at each point in time. In other embodiments, the audio may be stored and/or processed as separate signals, channels or files for different individual speakers from among clinical personnel 220, and/or for different groups of speakers among clinical personnel 220. For instance, audio of the primary surgeon speaking may be stored and/or processed separately from audio of the anesthesiologist speaking, and audio of nurses or other non-physicians speaking may be stored and/or processed together with each other but separately from the physicians' audio. Each separate set of audio data may then be tagged with an identification of the speaker(s) represented by that data, e.g., through metadata associated with the audio. It should be appreciated that audio data may be separated or grouped in any suitable manner, as aspects of the invention are not limited in this respect. In addition, it should be appreciated that audio data, though separated to isolate the speech of a particular individual or group of individuals, may still contain audio picked up by the microphone(s) when other individuals were speaking, which may be viewed as a form of background noise for that particular separated signal.

In some embodiments, separate audio data may be stored and/or processed for the audio recorded by each microphone present in procedure room 280. When individual microphones are worn by or directed at particular individual speakers, this may serve to isolate those speakers' speech to a feasible degree. In some embodiments, grouped audio data from multiple microphones or audio data from a single microphone that received speech from multiple speakers may be labeled or otherwise tagged to designate portions of the audio data that were spoken by particular speakers. Speaker identification may be performed in any suitable way, as aspects of the invention are not limited in this respect. For example, speakers may be identified based on which microphone was closest to the speaker (e.g., which microphone picked up the speaker's speech the loudest or with greatest amplitude) during that portion of speech. In some embodiments, any of various multichannel signal processing techniques, such as beamforming, may be used to focus channels of the audio data on individual speakers. Alternatively or additionally, speakers may be identified based on any suitable automatic voice recognition techniques using acoustic qualities of individual speakers' voices, and/or based on peculiarities of word usage, accent, and/or any other suitable technique. However, in some embodiments no speaker identification may be performed at all.

In some embodiments, a transcriptionist 230 may receive the audio data recorded by recording component 210, and may transcribe it into a textual representation of the oral communication from the clinical procedure. Transcriptionist 230 may be any human who listens to the audio data and writes or types what was spoken into one or more text documents. In some embodiments, transcriptionist 230 may be specifically trained in the field of medical transcription, and may be well-versed in medical terminology. When transcriptionist 230 has completed the transcription of the oral communication into a textual representation, the resulting transcription may in some embodiments be transmitted to system 200 or to any other suitable location (e.g., to a storage location accessible to system 200). Specifically, in some embodiments the text transcription may be received from transcriptionist 230 by system 200 for processing by fact extraction component 204. Exemplary functionality of fact extraction component 204 is described below.

In some other embodiments, the audio data recorded by recording component 210 may be received, at system 200 or at any other suitable location, by ASR engine 202. In some embodiments, ASR engine 202 may then process the audio data to determine what was spoken. Such processing may involve any suitable automatic speech recognition technique, as aspects of the present invention are not limited in this respect. In some embodiments, the audio recording may be automatically transcribed (e.g., converted to a textual representation), while in other embodiments, words identified directly from the audio recording may be represented in a data format other than text, or abstract concepts may be identified instead of words. Examples of further processing are described below with reference to a transcription that is a textual representation of the oral communication; however, it should be appreciated that similar processing may be performed on other representations of the oral communication as discussed above. When a textual representation is produced, in some embodiments it may be reviewed by a human (e.g., a transcriptionist) for accuracy, while in other embodiments the output of ASR engine 202 may be accepted as accurate without human review. As discussed above, some embodiments are not limited to any particular method for transcribing audio data; oral communication from a clinical procedure may be transcribed manually by a human transcriptionist, automatically by ASR, or semiautomatically by human editing of a draft transcription produced by ASR. Transcriptions produced by ASR engine 202 and/or by transcriptionist 230 may be encoded or otherwise represented as data in any suitable form, as aspects of the invention are not limited in this respect.

In some embodiments, ASR engine 202 may make use of a lexicon of clinical terms (which may be part of, or in addition to, another more general speech recognition lexicon) while determining the sequence of words that were spoken in the oral communication during the clinical procedure. However, aspects of the invention are not limited to the use of a lexicon, or any particular type of lexicon, for ASR. When used, the clinical lexicon in some embodiments may be linked to a clinical language understanding ontology or other knowledge representation model utilized by fact extraction component 204, such that ASR engine 202 can produce a text transcription containing terms in a form understandable to fact extraction component 204. In some embodiments, a more general speech recognition lexicon may also be shared between ASR engine 202 and fact extraction component 204. However, in other embodiments, ASR engine 202 may not have any lexicon developed to be in common with fact extraction component 204. In some embodiments, a lexicon used by ASR engine 202 may be linked to a different type of clinical knowledge representation model, such as one not designed or used for language understanding. It should be appreciated that any lexicon used by ASR engine 202 and/or by fact extraction component 204 may be implemented and/or represented as data in any suitable way, as aspects of the invention are not limited in this respect.

As discussed above, in some embodiments the audio data received by ASR engine 202 may be configured such that portions of the oral communication spoken by different speakers during the clinical procedure can be distinguished from each other. For example, audio portions spoken by different speakers may be stored as separate audio files or received as separate channels, or portions of the same audio file spoken by different speakers may be labeled, tagged or otherwise marked to identify which speaker was speaking. In some embodiments, ASR engine 202 may make use of this information to improve the speech recognition process. For example, ASR engine 202 may apply different acoustic models and/or language models to the recognition of speech from different speakers. In some embodiments, such speech recognition models may be speaker-specific, with each model being trained to recognize the speech of a particular speaker. In other embodiments, speech recognition models may be specific to particular types of speakers. For example, acoustic models may be specific to gender, and/or to any other suitable characteristic tending to produce predictable acoustic differences in speech. In some embodiments, language models may be specific to speakers' job categories, to reflect the tendency for personnel with different roles in the clinical procedure to use different words and/or phrases. For example, a different language model may be used for the surgeon than for the anesthesiologist, and another different language model may be used for nurses and/or other non-physicians. Alternatively or additionally, language models may be specific to particular procedures or categories of procedures. For example, the language model(s) used for an appendectomy procedure may be different from the language model(s) used for a hip replacement or an open heart surgery.

Such diversification of speech recognition models may be employed in any suitable combination, as aspects of the invention are not limited in this respect. In one example, each individual speaker may have a set of different speaker-specific models for different types of procedures. In another example, acoustic models may be speaker specific while language models may only be specific to job and/or procedure category. In yet another example, a number of different models with various levels of specificity may be utilized for physicians, while fewer and more generic models may be used for nurses and/or other non-physicians. Any other suitable criteria for diversifying speech recognition models may also be employed. For instance, language model(s) utilized for a current clinical procedure may be adapted based on the names of the clinical personnel performing the current procedure, the name of the patient and/or any relevant information in the patient's medical history. For example, data on the patient's gender may be used to bias the language model away from names of organs or other words specific to the opposite gender. Data on symptoms, diagnoses and/or other medical history information specific to the current patient may also be used to bias the language model. However, in some other embodiments, speech recognition models may not be specific at all to speaker, job category, procedure category, patient characteristics and/or any other criteria.

In some embodiments, ASR engine 202 may produce a text transcription that includes or is otherwise associated with timing information detailing the points in time at which various portions of the oral communication were spoken during the clinical procedure. Such timing information in some embodiments may be encoded as metadata such as timestamps associated with the transcription, and/or may be embedded as labels in the transcription itself, or any other suitable technique may be used for associating timing information with such a transcription. Similarly, in some embodiments a transcription produced by transcriptionist 230 may also have associated timing information indicating the time during the clinical procedure at which portions of the oral communication were spoken. Such timing information may be captured in any suitable way. For example, in some embodiments transcriptionist 230 may use an interface that allows him or her to manually associate particular portions of the text transcription with particular portions of the audio recording, or an electronic system used by transcriptionist 230 may automatically associate timing information with the transcription with reference to the portion of the audio data being played back as the transcriptionist enters text into the system. Timing information associated with a transcription produced by transcriptionist 230 or ASR engine 202 may be encoded and/or otherwise represented as data in any suitable form, as aspects of the invention are not limited in this respect. In addition, timing information may be included at any suitable level of detail, including multiple levels, as aspects of the invention are not limited in this respect. For example, timestamps may be generated for the transcription at the level of transitions between the speech of different speakers within the audio data, at the level of significant pauses in the recorded speech, at the level of utterances, sentences, phrases, words, syllables, individual phonemes and/or any other suitable interval. In another example, timestamps may be included at fixed intervals of time during the audio recording (e.g., every second, or any other suitable time interval), and each timestamp may be aligned with whatever word or other element in the text transcription was said at the time represented by the timestamp.

In some embodiments, monitoring equipment 252 may also be present in procedure room 280 and may, for example, collect physiological data from patient 222 during the clinical procedure. For example, monitoring equipment 252 may monitor physiological data such as heart rate, blood pressure, respiratory rate, oxygen saturation, body temperature, and/or any other suitable physiological data (which may vary as appropriate based upon circumstances such as characteristics of the patient and/or the procedure being performed). Alternatively or additionally, monitoring equipment 252 may make other measurements such as the amount of drugs, fluids, etc., that are administered to the patient during the clinical procedure. However, aspects of the invention are not limited to the use of any particular monitoring data. In some embodiments, monitoring data produced by monitoring equipment 252 may be collected and/or stored by monitoring component 250, which may be implemented locally to procedure room 280, remotely at system 200, or in any other suitable configuration. Monitoring component 250 may be implemented in any suitable form, including as hardware, software, or a combination of hardware and software, and may include dedicated recording circuitry and/or one or more processors programmed to record (e.g., store) monitoring data received from monitoring equipment 252. The monitoring data may be represented in any suitable form and may be encoded in any suitable data format, as aspects of the invention are not limited in this respect. In some embodiments, monitoring component 250 may also associate timing information with the recorded monitoring data. For example, if monitoring data is sampled at discrete intervals in time, the sampling rate may be included, along with the starting time and/or ending time of the monitoring, in the monitoring data compiled by monitoring component 250, to allow for calculation of the time at which particular events occurred in the monitoring data. Monitoring component 250 may also, in some embodiments, label significant events in the monitoring data with particular time indices, such as points in time at which the patient's heart rate dropped below a predetermined threshold, for example.

In some embodiments, the text transcription of the oral communication transcribed by ASR engine 202 and/or by transcriptionist 230, and optionally the monitoring data collected by monitoring component 250, may be processed by fact extraction component 204. Such data may be transmitted or otherwise made accessible to fact extraction component 204 via any suitable form of local and/or network connection(s), and/or by communication between hardware and/or software modules of a common device upon which the components involved may be implemented. In some embodiments, fact extraction component 204 may perform processing (e.g., by operation of the one or more processors of system 200 to implement instructions stored in a memory of system 200) to extract one or more clinical facts from the transcription. As one example, if the transcription includes a statement, "I'm now lysing the adhesion," spoken by the surgeon, fact extraction component 204 may extract a clinical fact such as, "adhesion was lysed," from this portion of the transcription.

Any suitable technique(s) for extracting clinical facts from the text transcription may be used, as aspects of the present invention are not limited in this respect. In some embodiments, fact extraction component 204 may be implemented using techniques such as those described in U.S. Pat. No. 7,493,253, entitled "Conceptual World Representation Natural Language Understanding System and Method." This patent is incorporated herein by reference in its entirety. Such a fact extraction component 204 may make use of a formal ontology linked to a lexicon of clinical terms. The formal ontology may be implemented as a relational database, or in any other suitable form, and may represent semantic concepts relevant to the clinical domain, as well as linguistic concepts related to ways the semantic concepts may be expressed in natural language.

In some embodiments, concepts in a formal ontology used by fact extraction component 204 may be linked to a lexicon of clinical terms and/or codes, such that each clinical term and each code is linked to at least one concept in the formal ontology. In some embodiments, the lexicon may include the standard clinical terms and/or codes used by the institution in which fact extraction component 204 is applied. In some embodiments, the lexicon may also include variations on the standard clinical terms and/or additional clinical terms used by clinical personnel in oral communication during clinical procedures. Such additional clinical terms may be linked, along with their corresponding standard clinical terms, to the appropriate shared concepts within the formal ontology. For example, the standard term "cardiac arrest" as well as other orally used terms such as "crashing" and "coding" may all be linked to the same abstract concept in the formal ontology—a concept representing cessation of heart beat.

In some embodiments, a formal ontology used by fact extraction component 204 may also represent various types of relationships between the concepts represented. One type of relationship between two concepts may be a parent-child relationship, in which the child concept shares attributes of the parent concept as well as additional attributes. In some embodiments, any other type(s) of relationship useful to the process of clinical documentation may also be represented in the formal ontology. For example, one type of relationship may be a complication relationship. In one example of a complication relationship, a concept linked to the term "pneumothorax" (collapsed lung) may have a relationship of "is-complication-of" to the concept linked to the term "pacemaker implantation" (a type of surgical procedure). This relationship may represent the knowledge that pneumothorax is a known complication of pacemaker implantations. Any number and type(s) of concept relationships may be included in such a formal ontology, as aspects of the present invention are not limited in this respect.

In some embodiments, automatic extraction of clinical facts from a text transcription may involve parsing the transcription to identify clinical terms that are represented in the lexicon of fact extraction component 204. Concepts in the formal ontology linked to the clinical terms that appear in the transcription may then be identified, and concept relationships in the formal ontology may be traced to identify further relevant concepts. Through these relationships, as well as the linguistic knowledge represented in the formal ontology, one or more clinical facts may be extracted. In some embodiments, relationships between concepts in the formal ontology may also allow fact extraction component 204 to automatically extract facts containing clinical terms that were not explicitly stated in the oral communication that was transcribed.

For instance, in one example, oral communication during a pacemaker implantation procedure may contain a statement from one of the clinical personnel: "The patient's lung is collapsing." Fact extraction component 204 may search the lexicon for recognized words such as "lung" and "collapsing." These words may be linked together to the concept "pneumothorax" in the ontology, from which fact extraction component 204 may extract the fact that a pneumothorax has occurred. Further, the concept "pneumothorax" may be linked in the ontology to the concept "pacemaker implantation" via the relationship "is-complication-of." By tracing this relationship, fact extraction component 204 may extract the more specific fact that a pneumothorax has occurred as a complication of the pacemaker implantation procedure. Then, as discussed below, this fact may be incorporated into an automatically generated operative report, e.g., by listing "Pneumothorax" in a section with heading "COMPLICATIONS."

It should be appreciated that the foregoing descriptions are provided by way of example only, and that any suitable technique(s) may be used for extracting a set of one or more clinical facts from a text transcription of oral communication during a clinical procedure, as aspects of the present invention are not limited to any particular fact extraction technique. For instance, it should be appreciated that fact extraction component 204 is not limited to the use of an ontology, as other forms of knowledge representation models, including statistical models and/or rule-based models, may also be applicable. The knowledge representation model may also be represented as data in any suitable format, and may be stored in any suitable location, such as in a memory of system 200 accessible by fact extraction component 204, as aspects of the invention are not limited in this respect. In addition, a knowledge representation model such as an ontology used by fact extraction component 204 may be constructed in any suitable way, as aspects of the invention are not limited in this respect.

For instance, in some embodiments a knowledge representation model may be constructed manually by one or more human developers with access to expert knowledge about clinical procedures, their constituent steps, associated diagnoses, potential complications, appropriate observations and/or clinical findings, and/or any other relevant information. In other embodiments, a knowledge representation model may be generated automatically, for example through statistical analysis of past operative reports, of transcriptions of oral communication during clinical procedures, and/or of other medical documents. Thus, in some embodiments, fact extraction component 204 may have access to a data set 270 of medical literature and/or other documents such as past operative reports and/or transcriptions. In some embodiments, past reports, transcriptions and/or other text documents may be marked up (e.g., by a human) with labels indicating the nature of the relevance of particular statements in the text to the clinical procedure(s) to which the text relates. A statistical knowledge representation model may then be trained to form associations based on their prevalence within an aggregate set of multiple marked up documents. For example, if "pneumothorax" is labeled as a "complication" in a large enough proportion of operative reports documenting pacemaker implantation procedures, a statistical knowledge representation model may generate and store a concept relationship that "pneumothorax is-complication-of pacemaker implantation." In some embodiments, automatically generated and hard coded (e.g., by a human developer) concepts and/or relationships may both be included in a knowledge representation model used by fact extraction component 204.

As discussed above, it should be appreciated that aspects of the invention are not limited to any particular technique(s) for constructing knowledge representation models. Examples of suitable techniques include those disclosed in the following Gómez-Pérez, A., and Manzano-Macho, D. (2005). *An overview of methods and tools for ontology learning from texts*. Knowledge Engineering Review 19, p. 187-212.

Cimiano, P., and Staab, S. (2005). *Learning concept hierarchies from text with a guided hierarchical clustering algorithm*. In C. Biemann and G. Paas (eds.), Proceedings of the ICML 2005 Workshop on Learning and Extending Lexical Ontologies with Machine Learning Methods, Bonn, Germany.

Fan, J., Ferrucci, D., Gondek, D., and Kalyanpur, A. (2010). *PRISMATIC: Inducing Knowledge from a Lange Scale Lexicalized Relation Resource*. NAACL Workshop on Formalisms and Methodology for Learning by Reading.

Welty, C., Fan, J., Gondek, D. and Schlaikjer, A. (2010). *Large scale relation detection*. NAACL Workshop on Formalisms and Methodology for Learning by Reading.

Each of the foregoing publications is incorporated herein by reference in its entirety.

In another example, fact extraction component 204 may utilize a statistical knowledge representation model based on entity detection and/or tracking techniques, such as those disclosed in: Florian, R., Hassan, H., Ittycheriah, A., Jing, H., Kambhatla, N., Luo, X., Nicolov, N., and Roukos, S. (2004). *A Statistical Model for Multilingual Entity Detection and Tracking*. Proceedings of the Human Language Technologies Conference 2004 (HLT-NAACL'04). This publication is incorporated herein by reference in its entirety.

For example, in some embodiments, a list of fact types of interest for generating clinical procedure reports may be defined, e.g., by a developer of fact extraction component 204. Such fact types may include, for example, diagnoses, procedures, procedure steps, observations, medications, problems, and/or any other suitable fact types. It should be appreciated that any suitable list of fact types may be utilized, and may or may not include any of the fact types listed above, as aspects of the invention are not limited in this respect. In some embodiments, spans of text in a set of sample transcriptions of oral communication during clinical procedures may be labeled (e.g., by a human) with appropriate fact types from the list. For example, if a sample transcription contains the statement, "I'm now lysing the omental adhesion," a human annotator may label the span, "lysing the omental adhesion," with the "procedure step" fact type label. A statistical model may then be trained on the corpus of labeled sample transcriptions to detect and/or track such fact types as semantic entities, using known entity detection and/or tracking techniques.

In some embodiments, a statistical model may also be trained to associate fact types extracted from new transcriptions with particular facts to be used in generating a clinical procedure report. For example, in some embodiments, the human annotator may label "lysing the omental adhesion" not only with the "procedure step" fact type label, but also with a label indicating the particular procedure to which this step belongs (e.g., "lysis of adhesions") and/or the particular procedure step fact that the text indicates (e.g., "lysis of omental adhesion"). In such embodiments, for example, a single statistical model may be trained to detect and/or track specific particular facts as individual entities. However, in other embodiments, the process of detecting and/or tracking fact types as entities may be separated from the process of relating detected fact types to particular facts. For example, in some embodiments, a separate statistical model may be trained on different training data to take as input spans such as "lysing the omental adhesion," previously labeled with the "procedure step" fact type label, and relate them to the particular procedure "lysis of adhesions" and/or to the particular fact "lysis of omental adhesion." In other embodiments, such a relation model may be hard-coded and/or otherwise rule-based, while the entity detection and/or tracking model used to extract fact types from text spans may be trained statistically.

It should be appreciated that the foregoing are merely examples, and that fact extraction component 204 may be implemented in any suitable way and/or form, as aspects of the invention are not limited in this respect.

In some embodiments, different full knowledge representation models may be constructed for different types of clinical procedures, or different partial knowledge representation models specific to particular procedures may be accessed selectively in conjunction with a generic knowledge representation model. In other embodiments, a single knowledge representation model may be constructed with concepts and relationships adequate to address all clinical procedures for which the knowledge representation model is used, and the relationships stored may determine the likelihood with which certain concepts are activated in the context of a particular procedure.

In some embodiments, a knowledge representation model or portion of a knowledge representation model may be made specific to a particular type of procedure by training it on transcriptions, operative reports and/or other medical documents specific to that type of procedure. In one example, operative report 100 documenting an appendectomy procedure, once approved by a responsible clinician, may be used to train a knowledge representation model on concepts and associations relevant to appendectomies. For example, if the statements, "omental adhesion," "partial closed loop small-bowel obstruction," and "ischemic bowel" are labeled in section 112 of the appendectomy report as "observations," the knowledge representation model may learn that these concepts are relevant clinical observations for appendectomy procedures. Mark-up of section 130 of example operative report 100 may also aid in training the knowledge representation model on the procedural steps involved in an appendectomy and the order in which they are performed: "anesthesia," followed by "prepped and draped," then "incision," "suctioning," etc. As an alternative or in addition to the process of (e.g., manual) mark-up of documents for model training, section headings within the documents may also be used in building associations. For example, the term "Foley catheter" in section 118 may be learned as a relevant "drain" for an appendectomy procedure, because of the section heading, "DRAINS."

In some embodiments, a knowledge representation model used by fact extraction component 204 may also be trained on (and/or may be linked to a separate model component trained on) transcriptions of oral communication spoken during past clinical procedures. Such model training may allow fact extraction component 204 to extract clinical facts from oral communication transcriptions despite the varied ways in which clinical personnel may speak about such information during a procedure, which may be quite different from the type of language used in operative reports and/or in medical literature. For example, when speaking to each other about a patient who is experiencing excessive bleeding during a surgical procedure, clinical personnel may speak such varied utterances as, "Blood pressure is dropping," "We've got a bleeder here," "We need to ligate quickly," "I'm clamping," and, "Where's it coming from?" In some embodiments, any of such similar statements in a transcription of oral communication from a past clinical procedure may be labeled (e.g., manually) as indicative of "excessive bleeding" or "hemorrhage." Further, "excessive bleeding" and/or "hemorrhage" may also be labeled as "complications" of the surgical procedure corresponding to the transcription. Such labeled text may then be used to train fact extraction component 204 (e.g., by training the model(s) utilized by fact extraction component 204) to extract a clinical fact related to "hemorrhage" as a "complication" from such statements in future transcriptions for that clinical procedure, and/or from combinations of such statements with high likelihood of "hemorrhage"-related labels in the training data.

In some embodiments, rather than receive a complete transcription of the entire oral communication from a current clinical procedure from ASR engine 202 before performing any fact extraction, fact extraction component 204 may perform some of its processing concurrently with ASR engine 202 on a current clinical procedure transcription. For instance, the inventor has recognized that typical words and/or phrases spoken by clinical personnel 220 may change in predictable ways between different stages of a clinical procedure. To take advantage of this predictability, in some embodiments different language models may be trained for different stages of a clinical procedure, and/or a language model may be trained to apply different statistics to different stages of the clinical procedure. In some embodiments, ASR engine 202 may be informed by fact extraction component 204 as to what is the current stage of the clinical procedure for each portion of the audio data, and may apply its language models to the speech recognition accordingly. In one example, ASR engine 202 may initially transcribe a first portion of the audio data using a generic language model, and may pass the partial transcription to fact extraction component 204. Fact extraction component 204 may then extract one or more clinical facts from the first portion of the audio data, and may determine from the extracted fact(s) what stage of the procedure was being performed. This information may be relayed back to ASR engine 202, which may then transcribe the next portion of the audio data using the language model(s) appropriate for that stage of the procedure. In another example, ASR engine 202 may by default apply a "preparation" language model to the first portion of the audio data for, e.g., a surgical procedure, based on the assumption that most surgeries begin with a preparation stage. Fact extraction component 204 may then extract clinical facts from each portion of the transcription as it is provided by ASR engine 202, and may alert ASR engine 202 when sufficient facts have been extracted to indicate that a transition, e.g., from the preparation stage to the incision stage, has occurred or will soon occur. ASR engine 202 may then switch to an "incision" language model for recognizing subsequent portions of the oral communication. However, it should be appreciated that certain aspects of the invention are not limited to any particular language modeling techniques, and some embodiments may not include the use of multiple stage-specific language models.

As discussed above, audio data (e.g., collected by recording component 210) may in some embodiments be labeled or otherwise marked with identification of which speaker was talking during various portions of the oral communication. In some embodiments, the transcription of the oral communication produced by ASR engine 202 and/or by transcriptionist 230 may also have portions marked by speaker, as their corresponding portions in the audio data were. In some embodiments, fact extraction component 204 may use this information to inform its extraction of clinical facts from the transcription. For example, a mention of a dosage amount by the anesthesiologist may give rise to extraction of a fact that that amount of anesthetic was administered to the patient during the clinical procedure, while a similar utterance by different personnel may not give rise to extraction of such a fact.

In some embodiments, fact extraction component 204 may also receive monitoring data collected by monitoring component 250, and may use this monitoring data to extract clinical facts for documenting the clinical procedure, independently of the transcribed oral communication. For example, monitoring data collected by monitoring component 250 may provide the measure of 100 mL of estimated blood loss documented in section 120 of example operative report 100. In addition, in some embodiments monitoring data collected by monitoring component 250 may inform the extraction of clinical facts from the transcription of the oral communication. In some embodiments, the oral communication and the monitoring data may be integrated by synchronizing the timing information associated with each. For example, if the monitoring data indicates the occurrence of a significant event (e.g., a sudden drop in blood pressure, heart rate or other physiological measure) at a particular time index during the clinical procedure, fact extraction component 204 can then search within the vicinity of that time index in the transcription and/or the audio data for clinical facts that may be extracted to explain the event reflected in the monitoring data. In some cases, certain statements in the transcription may have different connotations and/or different significance when viewed in light of concurrently recorded monitoring data than when viewed in isolation. In some embodiments, timing information associated with the transcription, with the audio data and/or with the monitoring data may also be used by fact extraction component 204 to determine the duration of the procedure and/or of any of its constituent parts or steps. Such objective determination of duration information may in itself represent a significant step forward in clinical procedure documentation practices, which conventionally must rely upon the memory of the physician for documentation of the approximate durations of individual parts of the procedure.

In some embodiments, fact extraction component 204 may also have access to a data set 260 of patient history records, from which it may access the medical history for the patient upon which the current clinical procedure was performed. In some cases, much of the general information needed for documenting the clinical procedure may be available directly from the patient's medical chart and/or electronic health record, or from extracting facts from past narrative documentation within the patient's chart. Such information may include the patient's name, preoperative diagnosis, indication for operation, drugs administered preoperatively, and/or any other suitable information documented prior to the clinical procedure. In addition, information from the patient's records may also be used by fact extraction component 204 in some embodiments to inform the clinical facts that it extracts from the transcription of the oral communication spoken during the clinical procedure. For example, certain clinical findings, complications, comorbidities, etc., may be more likely during the clinical procedure based on the patient's known presenting symptoms, preoperative diagnosis and/or medical history, and fact extraction component 204 may interpret statements in the oral communication accordingly. As discussed above, the patient's history records or facts extracted from such records may also be used by ASR engine 202 to select and/or modify the language model(s) it uses in transcribing the audio data.

As should be appreciated from the foregoing, the extraction of clinical facts from a transcription of oral communication spoken during a clinical procedure in some embodiments may involve distinguishing relevant information from non-relevant information in the transcription. For example, a surgeon's conversation with his assistant during a surgical procedure about what he did for fun over the past weekend is not likely to be relevant for documenting the surgical procedure. It also is not likely to correspond to clinical concepts in a knowledge representation model used by fact extraction component 204, and therefore not likely to be extracted from the transcription as a clinical fact. In addition, in some embodiments, having extracted multiple clinical facts from the transcription of the oral communication, from the monitoring data, and/or from patient history records 260, fact extraction component 204 may then filter the extracted clinical facts to determine which facts are relevant for documenting the clinical procedure. For example, the knowledge representation model may indicate that a certain amount of bleeding is routinely expected in certain types of surgical procedures, but is a notable complication in other types of surgical procedures. Thus, for the types of procedures for which bleeding is routine, certain extracted facts related to bleeding may be determined not to be relevant to documenting that procedure, and fact extraction component 204 in some embodiments may therefore filter those facts out of the set of facts that will be used to create the operative report. However, in other embodiments, extracted clinical facts may be retained despite having less relevance to the current clinical procedure, to err on the side of inclusiveness rather than omission. Further, in some embodiments fact extraction component 204 may make determinations as to which extracted facts are relevant and therefore to be retained for documentation based on one or more applicable report content standards, which may suggest and/or require certain information to be documented in a clinical procedure report, as discussed above.

In some embodiments, a set of relevant clinical facts extracted by fact extraction component 204 may be added as discrete structured data items to a structured data repository such as an electronic health record (EHR) for the patient. However, in other embodiments, relevant extracted clinical facts may be alternatively or additionally received from fact extraction component 204 by report generation component 206. Such data may be transmitted to report generation component 206 via any suitable form of local and/or network connection(s), and/or by communication between hardware and/or software modules of a common device upon which the components involved may be implemented. In some embodiments, report generation component 206 may perform processing (e.g., by operation of one or more processors of system 200 to execute instructions stored in a memory of system 200) to automatically generate a text report (such as an operative report) from the relevant clinical facts extracted by fact extraction component 204 from the transcription of the oral communication spoken during the clinical procedure. In some embodiments, the text report may document the clinical procedure at least partially in narrative natural language format, e.g., detailing multiple steps of the procedure through semantically connected sentences having a narrative flow. An example of this type of narrative natural language format is illustrated in sections 110, 112 and 130 of example operative report 100 in FIG. 1; however, this is just one example, and aspects of the invention are not limited to this particular form of operative report.

In some embodiments, a report generation model used by report generation component 206 to automatically generate text reports may be constructed manually, e.g., by one or more human experts. In other embodiments, the report generation model may be trained statistically on the same or a similar set of past clinical procedure reports (e.g., accessed from medical document data set 270) as is used to train the knowledge representation model used by fact extraction component 204. For example, in some embodiments the past text reports that are marked up with clinical facts to associate with particular portions of text may also be marked up by a syntactic and/or grammatical parser, to train the report generation model on the way clinical facts are expressed in natural language sentences in the context of other surrounding sentences. While fact extraction component 204 may use text training data to learn how to extract discrete structured clinical facts from free-form oral communication, report generation component 206 may use similar training data to, in a sense, "work backward" from the discrete structured facts to generate a natural language narration typical of an operative report. In some embodiments, report generation component 206 may also use one or more report generation models that are specific to generating reports for particular clinicians who will ultimately review and/or authorize the reports. Such report generation models may be trained, for example, on past clinical procedure reports that were written, dictated, edited or otherwise reviewed and/or authorized by the corresponding clinician, and/or may be trained and/or retrained as the clinician continues to authorize new reports, as discussed below. In some embodiments, a report generation model may be partially statistically trained and partially manually constructed.

In some embodiments, report generation component 206 may also access patient history records 260 for information to be included in the text report documenting the clinical procedure. In some cases, certain sections and/or portions of the text report may simply be copied from past narrative reports that are already part of the patient's medical record. For example, section 110 of example operative report 100, relating the indication for operation, may already have been created in documenting a past clinical encounter with the patient, and in that case may be copied directly from such past documentation. In some cases, texts portions of smaller sizes, such as individual sentences or phrases, may be copied from past reports from the patient's history and/or from other stored medical documents. For example, the report generation model may be trained that a particular clinician usually expresses a particular clinical fact using a particular sentence or phrase. In other cases, data from patient history records 260 may be applied to the report generation model as discrete clinical facts (e.g., stored as such in patient history records 260, or extracted from patient history records 260 by fact extraction component 204), and the report generation model may create natural language text corresponding to the facts to populate the text report.

In some embodiments, report generation component 206 may begin a process of generating a text report to document a clinical procedure, by identifying a set of report sections appropriate and/or required for documenting the particular clinical procedure at hand. This may be done in any suitable way. In some embodiments, an applicable report content standard may dictate a set of sections to be included in a report documenting a particular type of clinical procedure. In some embodiments, report generation component 206 may be programmed with a default set of sections for any suitable criteria. For example, a default set of sections may be specified for clinical procedures in general, or different sets of sections may be specified for surgical procedures than for pathology procedures or other types of procedures, or different sets of sections may be specified for different types of surgical procedures (such as appendectomies), or different sets of sections may be specified for reports produced for different clinicians, or for different institutions, or for any other suitable categorization of clinical procedure reports. As an example, operative report 100 depicted in FIGS. 1A-1C includes the set of sections {"PREOPERATIVE DIAGNOSIS," "POSTOPERATIVE DIAGNOSIS," "NAME OF PROCEDURE," "SURGEON," "ASSISTANT," "ANESTHESIOLOGIST," "ANESTHESIA," "INDICATION FOR OPERATION," "OPERATIVE FINDINGS," "GRAFTS," "SPECIMENS," "DRAINS," "ESTIMATED BLOOD LOSS," "DEEP VEIN THROMBOSIS PROPHYLAXIS," "ANTIBIOTICS," "COMPLICATIONS," "SPONGE, NEEDLE, AND INSTRUMENT COUNT," "DESCRIPTION"}

In some embodiments, report generation component 206 may determine which facts of the set of clinical facts to be included in the report should be included in which sections of the set of report sections identified for the report, using any suitable technique(s). In some embodiments, report generation component 206 may be programmed with a set of rules that associate particular clinical facts, or particular types of clinical facts, with particular sections of a clinical procedure report. In some embodiments, such rules may be represented as part of a knowledge representation model such as an ontology. In some embodiments, report generation component 206 may be trained statistically to assign clinical facts to report sections. For example, in some embodiments, clinical facts may be extracted from a training set of past clinical procedure reports, and the report sections from which those clinical facts were extracted may be used to train report generation component 206 to determine the best report sections in which to include new clinical facts for new reports.

In some embodiments, report generation component 206 may be configured to determine an order in which to include multiple clinical facts within a particular section of a clinical procedure report. For example, in some embodiments, report generation component 206 may make use of the timing information associated with particular clinical facts by other system components, and may order the clinical facts in temporal order within a report section. Alternatively or additionally, in some embodiments report generation component 206 may make use of a knowledge representation model such as an ontology, or other specified rules indicating that certain clinical facts can only occur after other clinical facts. For instance, in one example, a rule may specify that a complication of a surgical procedure can only occur after the surgical procedure has been initiated. It should be appreciated that report generation component 206 may order clinical facts in any suitable way, as aspects of the invention are not limited in this respect.

In some embodiments, report generation component 206 may then generate natural language sentences to represent the ordered clinical facts within the set of report sections for the clinical procedure report. Natural language generation (NLG) may be performed in any suitable way, as aspects of the invention are not limited in this respect. In some embodiments, known NLG techniques may be adapted to produce clinical procedure reports. Exemplary NLG techniques are disclosed in: Reiter, E., and Dale, R. (2000). *Building Natural Language Generation Systems*. Cambridge: Cambridge University Press. This publication is incorporated herein by reference in its entirety.

Other NLG techniques may also be used. In some embodiments, report generation component 206 may be programmed with specified individual sentences to use to represent particular individual clinical facts. Alternatively or additionally, in some embodiments report generation component 206 may be programmed to combine multiple facts into the same sentence. This may be done in any suitable way. For example, in some embodiments, report generation component 206 may be programmed with multiple-fact sentence templates with slots to be filled by particular clinical facts. In one example, report generation component 206 may be programmed with a sentence template, "The patient is a(n) X-year-old Y," where X and Y are slots to be filled by the patient's age fact and gender fact (male or female), respectively. Report generation component 206 may be programmed to use "a" or "an" depending on whether the fact inserted in slot X begins with a consonant or a vowel. In another example, report generation component 206 may be programmed with a sentence template, "A(n) X-catheter was inserted in the Y," where X is filled with a catheter type, such as "Pigtail," "Foley," "French Foley," or "triple lumen," and Y is filled with a body part, such as "urinary bladder," or "femoral artery." In some embodiments, report generation component 206 may be programmed to combine facts of similar types into the same sentence. For example, instead of producing separate sentences, "White blood cell count was 7.6," "Hemoglobin was 11.4," and "Platelet count was 37,000," report generation component 206 may be programmed to list the bloodwork facts together in a single sentence, such as, "White blood cell count was 7.6, hemoglobin was 11.4, and platelet count was 37,000." In some embodiments, complex sentences may be generated using a discourse planner to generate discourse specifications from clinical facts, and a surface realizer to generate sentences from discourse specifications. For example, a surface realizer could generate the sentence, "The aorta was dissected using a scalpel," from the discourse specification: {(process: dissect), (actee: aorta), (voice: passive), (tense: past), (means: scalpel)}. Many other examples are possible, and it should be appreciated that aspects of the invention are not limited to any particular implementation of NLG technique(s).

In some embodiments, a text report, once generated by report generation component 206, may be stored in patent history records 260, as part of the patient's medical record, and/or with medical literature/documents 270, for use in future research and/or in training and/or retraining models for the fact extraction and/or report generation processes. However, in other embodiments, a draft report may be provided for review by a user 242 prior to finalization and storage of the text report. User 242 may be one of clinical personnel 220, such as the primary physician responsible for the clinical procedure being documented, or may be a person other than a clinician, such as a report editing specialist. In some embodiments, both a non-clinician editor/reviewer and a physician may review and/or edit the text report, as described below.

In some embodiments, user 242 may review and/or edit the draft report generated by report generation component 206 through a user interface 240 provided in connection with system 200. Such a user interface may be implemented in any suitable way and/or form, as aspects of the invention are not limited in this respect. In one example, a user interface may be implemented using techniques disclosed in U.S. patent application Ser. No. 13/030,981, filed Feb. 18, 2011, entitled "Methods and Apparatus for Linking Extracted Clinical Facts to Text." This patent application is incorporated herein by reference in its entirety. In some embodiments, user interface 240 may be presented on a visual display. However, the user interface is not limited to a graphical user interface, as other ways of providing data to users from system 200 may be used. For example, in some embodiments, audio indicators and/or text-to-speech synthesis may be conveyed to user 242, e.g., via a speaker. It should be appreciated that any type of user interface may be provided in connection with report review and/or other related processes, as aspects of the invention are not limited in this respect.

In some embodiments, the draft report generated by report generation component 206 may be displayed or otherwise presented to user 242, who may be given the opportunity to edit the report. In some embodiments, a linkage may be maintained between each extracted clinical fact and the portion(s) of the transcription of the oral communication from which that fact was extracted, and/or between each corresponding portion of the draft text report and the portion(s) of the transcription of the oral communication from which the fact giving rise to that portion of the draft text report was extracted. For example, if a fact corresponding to "appendix not found" is extracted from statements in the transcription including, "I don't see the appendix," and in turn gives rise to generation of text in the narrative of the report including, "The appendix was searched for. The distal portion could not be found" (as illustrated in section 130 of example operative report 100), then a linkage may be maintained between each of the extracted fact, the corresponding portion of the transcription, and the corresponding portion of the text report. In some embodiments, while user 242 is reviewing the draft report via user interface 240 to report generation component 206, the system may provide one or more indicators to user 242 of the different linkages between various portions of the draft report, the different extracted facts from which they were generated, and/or the portions of the transcription from which the facts were extracted. Such indicators may be visual indicators, audio indicators, or any other suitable type of indicators, as aspects of the invention are not limited in this respect. In some embodiments, such linkage indicators may enhance the ability of user 242 to review the extracted facts and/or the corresponding portions of the draft report for accuracy, with reference to the specific parts of the oral communication that generated them. While some embodiments provide linkage information for each extracted fact, it should be appreciated that aspects of the invention relating to providing linkage information are not so limited, as linkage information may be provided for one or any subset of the extracted facts.

In some embodiments, user 242 may use user interface 240 to make changes to the draft report generated by report generation component 206. For example, user 242 may add text to the draft report and/or add facts to the set of clinical facts extracted by fact extraction component 204, may delete text from the draft report and/or delete facts from the set of clinical facts, and/or may modify text and/or facts displayed with the draft report. In some embodiments, such user edits may be provided as feedback to update and/or to re-train report generation component 206 and/or fact extraction component 204, which may result in some embodiments in user-specific fact extraction and/or report generation models. In some embodiments, user feedback may be used to adapt the models for more accurate fact extraction and/or report generation for the user's current editing session only, while in other embodiments, user-specific adapted models may be stored for future use for that user, and/or may be cumulatively adapted over time. Also, in some embodiments the feedback may be used to further modify the draft report and/or the set of extracted clinical facts. If user 242 makes changes to the set of extracted clinical facts, in some embodiments report generation component 206 may re-generate an updated text report from the new set of facts. The updated text report may then be returned to user 242 for further review, or stored as the final version of the text report. If user 242 makes changes to the text of the draft report, in some embodiments fact extraction component 204 may re-extract clinical facts from the new report, e.g., for inclusion in a discrete structured data repository such as the patient's EHR. However, not all embodiments may make use of user feedback, as aspects of the invention are not limited in this respect.

In some embodiments, automatically extracted and/or user-supplied clinical facts may also be automatically reviewed, and automatic alerts may be provided to user 242 if opportunities are identified for the documentation of the clinical procedure to be improved. Such alerts may be visual alerts, audio alerts, or any other suitable type of alerts, as aspects of the invention are not limited in this respect. For example, in some embodiments fact extraction component 204, report generation component 206 and/or any other suitable component of a procedure documenting system may be programmed based on an applicable standard specifying minimum information to be documented in a clinical procedure report, examples of which are discussed above. In some embodiments, when it is determined that additional information should be included in the text report to comply with one or more applicable standards (e.g., such as JCAHO or HL7), one or more prompts may be provided to user 242 to add information to the text report. Also, in some embodiments, a prompt may be provided when the system determines that disambiguation is desired between multiple facts that could potentially be extracted from the same portion of the oral communication during the clinical procedure. Furthermore, user 242 may choose for any suitable reason to add information to the text report, for example to supply additional details not captured by the oral communication during the procedure, and/or to document impressions, ideas and/or plans for future treatment that may have occurred to the physician after the procedure was over.

It should be appreciated that techniques described herein may be implemented in the context of various different workflows, as aspects of the invention are not limited in this respect. In some embodiments, review and/or editing of the text report may be performed entirely by a clinician or entirely by a non-clinician reviewer. In other embodiments, a non-clinician reviewer may edit the report in a first pass, and then the clinician may further edit and/or finalize the report. In still other embodiments, the clinician may make a first rough edit of the draft report, and then a non-clinician reviewer may formalize and/or finalize the report. In typical circumstances, a clinician such as the primary physician responsible for the clinical procedure will finalize, authorize and/or otherwise approve the text report, after which it will not be edited further. However, this is not required, and it should be appreciated that certain aspects of the invention are not limited to any particular reviewing and/or editing technique and/or configuration. Once approved, in some embodiments the text report documenting the clinical procedure may be stored with the patient's medical record, and/or may be included in a larger data set such as medical documents 270. In some embodiments, further fact extraction may be performed on the finalized procedure report, for purposes such as coding for billing, quality assurance review, etc.

Figure 3:
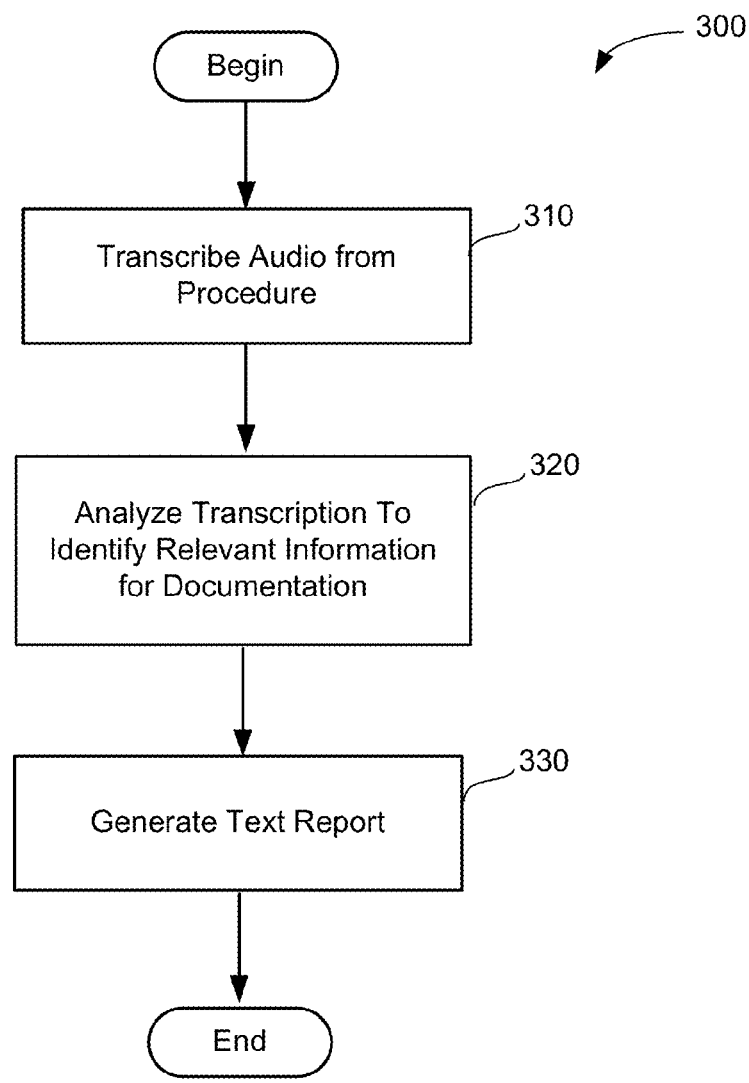
FIG. 3 is a flowchart illustrating an exemplary method for generating a report in accordance with some embodiments of the present invention.

It should be appreciated from the foregoing that one embodiment of the invention is directed to a method 300 for automatically generating a text report documenting a clinical procedure, as illustrated in FIG. 3. Method 300 may be performed, for example, by one or more components of a procedure documenting system 200 such as ASR engine 202, fact extraction component 204 and report generation component 206, although other implementations are possible, as method 300 is not limited in this respect. Method 300 begins at act 310, at which audio data comprising audio of one or more clinical personnel speaking while performing a clinical procedure may be transcribed, e.g., by automatic speech recognition or by a human transcriptionist. At act 320, the transcribed audio data may be analyzed to identify relevant information for documenting the clinical procedure. Method 300 ends at act 330, at which a text report including the relevant information documenting the clinical procedure may be automatically generated.

As discussed above, one type of clinical procedure that may be documented using techniques described herein is a surgical procedure; however, certain aspects of the present invention are not limited to surgical contexts. For example, another application for techniques described herein is in documenting sterile procedures in general. A surgical procedure may be one example type of sterile procedure. Another exemplary type of sterile procedure may be a clinical procedure performed on a patient in isolation in a hospital or other clinical institution, due to immunodeficiency, infectious disease, and/or any other suitable reason for isolating the patient. In the case of immunodeficiency, efforts are generally made to keep a clinician's hands/gloves (often in addition to other parts of the body and/or clothing) sterile when entering the room in which the patient is isolated. In the case of infectious disease, efforts are generally made to re-sterilize (or discard) anything worn and/or carried out of the patient's room after treatment of the patient. In each of these cases, the requirements of a sterile environment and/or hands-free performing of a procedure may make carrying around a hand-held recording device difficult and/or dangerous. Accordingly, techniques described herein, for example using sterile fixed microphones installed in the procedure room, may allow for unencumbered and uncontaminated performance of sterile procedures with relevant documentation information captured from oral communication that takes place during the procedure.

As discussed above, another exemplary application for techniques described herein may be in certain non-sterile clinical procedures such as resuscitation attempts conventionally requiring a core code reporter. For example, when a patient (e.g., in an ambulance, an emergency room, a hospital room, or any other suitable location) experiences cardiac arrest, attending clinical personnel will typically attempt to resuscitate the patient by "calling a code." Certain applicable standards require that an individual known as a "core code reporter" document the exact nature and timing of actions that are taken and events that occur during the resuscitation attempt. The inventor has recognized that techniques described herein may be applied to automatically generate such documentation from the oral communication that typically occurs during such a procedure. This may have the effect of lessening or perhaps even eliminating the need for a core code reporter to stand idly by performing documentation while a life-or-death emergency procedure is performed.

Another example type of clinical procedure may be a pathology procedure such as an autopsy, which is typically documented in a text report such as an autopsy report. During an autopsy, a pathologist typically documents each of his or her detailed findings and/or observations as he or she methodically dissects and analyzes the deceased's body. Such findings may be recorded using speech and a hand-held voice recorder; however, the use of the hand-held recording device may interfere with the pathologist's use of his or her hands during the autopsy. In some cases, an autopsy may need to be a sterile procedure, and use of a hand-held voice recorder may promote contamination of the sterile environment in proximity to the cadaver. By contrast, techniques described herein may be applied to allow the pathologist's hands to remain free (and in some cases sterile) during the procedure. In addition, pathologists conventionally write their own autopsy reports, using the recorded impressions only as a reminder of what to include manually in the report. By contrast, techniques described herein may be applied to at least partially automate the process of generating the text report, saving valuable time and effort for the pathologist. The pathologist may then be free to extemporize during the pathology procedure about his or her observations as they come to mind, without having to be concerned about the order, format or particular language of the resulting documentation, which may be generated automatically.

Figure 4:
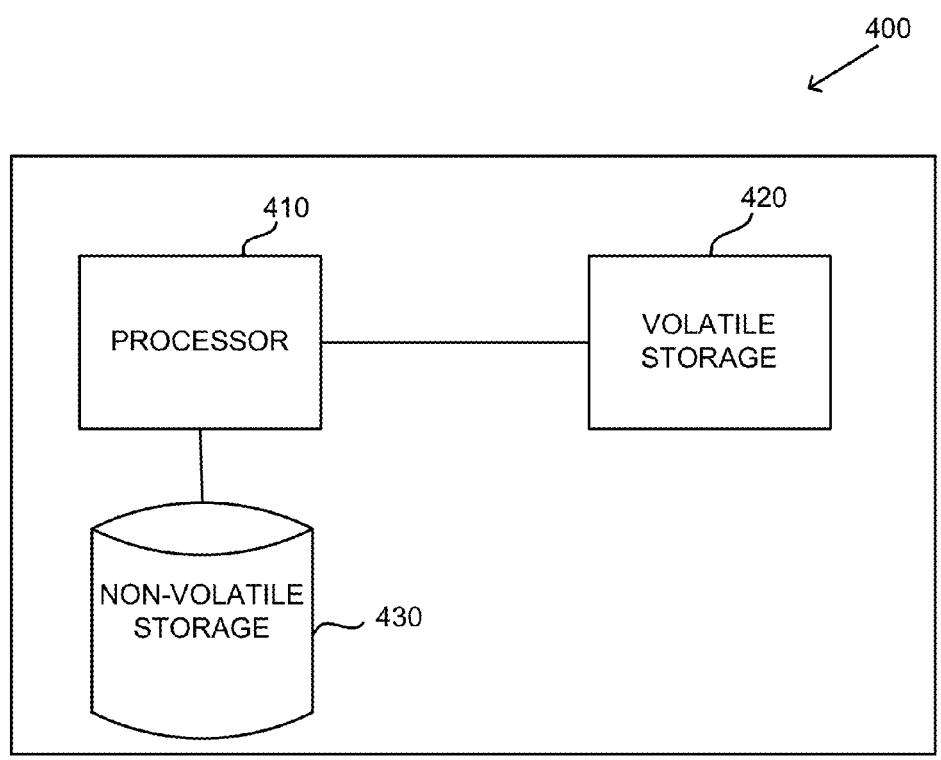
FIG. 4 is a block diagram illustrating an exemplary computer system on which aspects of the present invention may be implemented.

A clinical procedure documentation system in accordance with the techniques described herein may take any suitable form, as aspects of the present invention are not limited in this respect. An illustrative implementation of a computer system 400 that may be used in connection with some embodiments of the present invention is shown in FIG. 4. One or more computer systems such as computer system 400 may be used to implement any of the functionality described above. The computer system 400 may include one or more processors 410 and one or more tangible, non-transitory computer-readable storage media (e.g., volatile storage 420 and one or more non-volatile storage media 430, which may be formed of any suitable non-volatile data storage media). The processor 410 may control writing data to and reading data from the volatile storage 420 and/or the non-volatile storage device 430 in any suitable manner, as aspects of the present invention are not limited in this respect. To perform any of the functionality described herein, processor 410 may execute one or more instructions stored in one or more computer-readable storage media (e.g., volatile storage 420), which may serve as tangible, non-transitory computer-readable storage media storing instructions for execution by the processor 410.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of embodiments of the present invention comprises at least one computer-readable storage medium (e.g., a computer memory, a floppy disk, a compact disk, a magnetic tape, or other tangible, non-transitory computer-readable medium) encoded with a computer program (i.e., a plurality of instructions), which, when executed on one or more processors, performs above-discussed functions of embodiments of the present invention. The computer-readable storage medium can be transportable such that the program stored thereon can be loaded onto any computer resource to implement aspects of the present invention discussed herein. In addition, it should be appreciated that the reference to a computer program which, when executed, performs above-discussed functions, is not limited to an application program running on a host computer. Rather, the term "computer program" is used herein in a generic sense to reference any type of computer code (e.g., software or microcode) that can be employed to program one or more processors to implement above-discussed aspects of the present invention.

The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:
1. A method comprising:
   transcribing audio data comprising audio of one or more clinical personnel speaking while performing a sterile procedure, the audio data comprising audio of a first clinician speaking to one or more other clinical personnel while performing the sterile procedure, wherein transcribing the audio data comprises performing automatic speech recognition (ASR) on the audio data using a speech recognition model trained to recognize speech of the first clinician;
   analyzing the transcribed audio data, including the transcribed audio of the first clinician speaking to the one or more other clinical personnel while performing the sterile procedure, using at least one processor, to identify relevant information for documenting the sterile procedure, the analyzing comprising:

identifying within the transcribed audio data a statement made by the first clinician to the other clinical personnel while performing the sterile procedure, automatically determining whether information in the statement is relevant for documenting the sterile procedure, if it is determined that the information in the statement is relevant for documenting the sterile procedure, automatically designating the relevant information for inclusion in documentation of the sterile procedure, and if it is determined that the information in the statement is not relevant for documenting the sterile procedure, disregarding the statement in documenting the sterile procedure; and automatically generating a text report including the designated relevant information documenting the sterile procedure;

wherein determining that the information in the statement is relevant for documenting the sterile procedure comprises detecting in the statement a present-tense narration by the first clinician stating to the other clinical personnel that the first clinician is currently performing a particular step of the sterile procedure;

wherein automatically generating the text report comprises automatically transforming the present-tense narration into a non-present-tense text portion in the report, stating that the particular step of the sterile procedure was performed.

2. The method of claim 1, wherein the statement comprises the first clinician orally identifying an instrument being used in performing the sterile procedure, wherein the analyzing comprises automatically determining from the transcribed audio data a step of the sterile procedure performed using the instrument, and wherein generating the text report comprises automatically generating text stating that the step of the sterile procedure was performed using the instrument.

3. The method of claim 1, wherein the statement comprises the first clinician orally identifying an action being performed during the sterile procedure, wherein the analyzing comprises automatically determining whether the action is part of a step of the sterile procedure that is relevant for documenting the sterile procedure, and wherein generating the text report comprises, in response to determining that the action is part of a step of the sterile procedure that is relevant for documenting the sterile procedure, automatically generating text stating that the step was performed.

4. The method of claim 1, wherein the statement comprises the first clinician orally identifying an event occurring during the sterile procedure, wherein the analyzing comprises automatically determining whether the event indicates that a patient suffered a complication of the sterile procedure, and wherein generating the text report comprises, in response to determining that the event indicates that the patient suffered a complication of the sterile procedure, automatically generating text stating that the event occurred as a complication.

5. The method of claim 1, wherein the sterile procedure is performed on a patient, wherein the statement comprises the first clinician orally identifying one or more observations of a condition of the patient during the sterile procedure, wherein the analyzing comprises automatically determining whether the observed condition of the patient indicates that the patient suffered a complication of the sterile procedure, and wherein generating the text report comprises, in response to determining that the observed condition indicates that the patient suffered a complication of the sterile procedure, automatically generating text stating that the condition was observed as a complication.

6. The method of claim 1, wherein the sterile procedure is performed on a patient, wherein the statement comprises the first clinician orally identifying one or more substances administered to the patient in connection with the sterile procedure, and wherein generating the text report comprises automatically generating text stating that the one or more substances were administered.

7. The method of claim 1, further comprising recording the audio data through one or more microphones installed in a room in which the sterile procedure is performed.

8. The method of claim 1, further comprising recording the audio data through one or more microphones worn by the one or more clinical personnel.

9. The method of claim 1, wherein the ASR is performed using different speaker-specific models for audio produced by different speakers from among the one or more clinical personnel.

10. The method of claim 1, wherein the ASR is performed using a different language model for the sterile procedure than for a different sterile procedure.

11. The method of claim 1, wherein the sterile procedure is a first type of sterile procedure, and wherein the ASR is performed using a language model trained to be specific to the first type of sterile procedure.

12. The method of claim 1, further comprising allowing a human to verify accuracy of the ASR transcription before performing the analyzing.

13. The method of claim 1, wherein the analyzing is performed using at least one model trained on past sterile procedure reports, past audio transcriptions and/or medical literature.

14. The method of claim 1, wherein the analyzing is performed using a different model for the sterile procedure than for a different sterile procedure.

15. The method of claim 1, wherein the sterile procedure is a first type of sterile procedure, and wherein the analyzing is performed using a model trained to be specific to the first type of sterile procedure.

16. The method of claim 1, wherein the ASR is performed using different language models for different stages of the sterile procedure.

17. The method of claim 1, wherein the analyzing comprises identifying the relevant information based at least in part on rules regarding information to be documented for an institution responsible for the sterile procedure.

18. The method of claim 1, wherein the analyzing comprises identifying the relevant information based at least in part on identifying which portions of the audio were spoken by which of the one or more clinical personnel.

19. The method of claim 1, wherein the analyzing comprises determining, from the audio data, timing information for at least one step performed during the sterile procedure, and including the timing information in the relevant information.

20. The method of claim 1, wherein the analyzing comprises identifying the relevant information based at least in part on patient monitoring data recorded using monitoring equipment during the sterile procedure.

21. The method of claim 20, further comprising synchronizing timing information from the patient monitoring data with timing information from the audio data.

22. The method of claim 1, wherein the sterile procedure is performed on a patient, and wherein the analyzing comprises identifying the relevant information based at least in part on medical history data for the patient.

23. The method of claim 1, wherein the generating is performed using at least one model trained on past sterile procedure reports.

24. The method of claim 23, wherein the at least one model is specific to one of the one or more clinical personnel who authorizes the text report.

25. The method of claim 1, wherein the generating comprises copying text from at least one past medical report that also included the relevant information.

26. The method of claim 1, further comprising allowing a human user to make edits to the text report.

27. The method of claim 26, further comprising updating at least one model used in the generating based on the human user's edits to the text report.

28. The method of claim 26, further comprising prompting the human user to add information to the text report to comply with one or more report content standards.

29. The method of claim 1, wherein the sterile procedure is performed on a patient, and wherein the method further comprises including at least part of the relevant information in a discrete structured data repository for the patient.

30. Apparatus comprising:
at least one processor; and
at least one storage medium storing processor-executable instructions that, when executed by the at least one processor, perform a method comprising:
transcribing audio data comprising audio of one or more clinical personnel speaking while performing a sterile procedure, the audio data comprising audio of a first clinician speaking to one or more other clinical personnel while performing the sterile procedure, wherein transcribing the audio data comprises performing automatic speech recognition (ASR) on the audio data using a speech recognition model trained to recognize speech of the first clinician;
analyzing the transcribed audio data, including the transcribed audio of the first clinician speaking to the one or more other clinical personnel while performing the sterile procedure, to identify relevant information for documenting the sterile procedure, the analyzing comprising:
identifying within the transcribed audio data a statement made by the first clinician to the other clinical personnel while performing the sterile procedure,
automatically determining whether information in the statement is relevant for documenting the sterile procedure,
if it is determined that the information in the statement is relevant for documenting the sterile procedure, automatically designating the relevant information for inclusion in documentation of the sterile procedure, and
if it is determined that the information in the statement is not relevant for documenting the sterile procedure, disregarding the statement in documenting the sterile procedure; and
automatically generating a text report including the designated relevant information documenting the sterile procedure;
wherein determining that the information in the statement is relevant for documenting the sterile procedure comprises detecting in the statement a present-tense narration by the first clinician stating to the other clinical personnel that the first clinician is currently performing a particular step of the sterile procedure;
wherein automatically generating the text report comprises automatically transforming the present-tense narration into a non-present-tense text portion in the report, stating that the particular step of the sterile procedure was performed.

31. The apparatus of claim 30, wherein the statement comprises the first clinician orally identifying an instrument being used in performing the sterile procedure, wherein the analyzing comprises automatically determining from the transcribed audio data a step of the sterile procedure performed using the instrument, and wherein generating the text report comprises automatically generating text stating that the step of the sterile procedure was performed using the instrument.

32. The apparatus of claim 30, wherein the statement comprises the first clinician orally identifying an action being performed during the sterile procedure, wherein the analyzing comprises automatically determining whether the action is part of a step of the sterile procedure that is relevant for documenting the sterile procedure, and wherein generating the text report comprises, in response to determining that the action is part of a step of the sterile procedure that is relevant for documenting the sterile procedure, automatically generating text stating that the step was performed.

33. The apparatus of claim 30, wherein the statement comprises the first clinician orally identifying an event occurring during the sterile procedure, wherein the analyzing comprises automatically determining whether the event indicates that a patient suffered a complication of the sterile procedure, and wherein generating the text report comprises, in response to determining that the event indicates that the patient suffered a complication of the sterile procedure, automatically generating text stating that the event occurred as a complication.

34. The apparatus of claim 30, wherein the sterile procedure is performed on a patient, wherein the statement comprises the first clinician orally identifying one or more observations of a condition of the patient during the sterile procedure, wherein the analyzing comprises automatically determining whether the observed condition of the patient indicates that the patient suffered a complication of the sterile procedure, and wherein generating the text report comprises, in response to determining that the observed condition indicates that the patient suffered a complication of the sterile procedure, automatically generating text stating that the condition was observed as a complication.

35. The apparatus of claim 30, wherein the sterile procedure is performed on a patient, wherein the statement comprises the first clinician orally identifying one or more substances administered to the patient in connection with the sterile procedure, and wherein generating the text report comprises automatically generating text stating that the one or more substances were administered.

36. The apparatus of claim 30, wherein the method further comprises recording the audio data through one or more microphones installed in a room in which the sterile procedure is performed.

37. The apparatus of claim 30, wherein the method further comprises recording the audio data through one or more microphones worn by the one or more clinical personnel.

38. The apparatus of claim 30, wherein the ASR is performed using different speaker-specific models for audio produced by different speakers from among the one or more clinical personnel.

39. The apparatus of claim 30, wherein the ASR is performed using a different language model for the sterile procedure than for a different sterile procedure.

40. The apparatus of claim 30, wherein the sterile procedure is a first type of sterile procedure, and wherein the ASR is performed using a language model trained to be specific to the first type of sterile procedure.

41. The apparatus of claim 30, wherein the method further comprises allowing a human to verify accuracy of the ASR transcription before performing the analyzing.

42. The apparatus of claim 30, wherein the analyzing is performed using at least one model trained on past sterile procedure reports, past audio transcriptions and/or medical literature.

43. The apparatus of claim 30, wherein the analyzing is performed using a different model for the sterile procedure than for a different sterile procedure.

44. The apparatus of claim 30, wherein the sterile procedure is a first type of sterile procedure, and wherein the analyzing is performed using a model trained to be specific to the first type of sterile procedure.

45. The apparatus of claim 30, wherein the ASR is performed using different language models for different stages of the sterile procedure.

46. The apparatus of claim 30, wherein the analyzing comprises identifying the relevant information based at least in part on rules regarding information to be documented for an institution responsible for the sterile procedure.

47. The apparatus of claim 30, wherein the analyzing comprises identifying the relevant information based at least in part on identifying which portions of the audio were spoken by which of the one or more clinical personnel.

48. The apparatus of claim 30, wherein the analyzing comprises determining, from the audio data, timing information for at least one step performed during the sterile procedure, and including the timing information in the relevant information.

49. The apparatus of claim 30, wherein the analyzing comprises identifying the relevant information based at least in part on patient monitoring data recorded using monitoring equipment during the sterile procedure.

50. The apparatus of claim 49, wherein the method further comprises synchronizing timing information from the patient monitoring data with timing information from the audio data.

51. The apparatus of claim 30, wherein the sterile procedure is performed on a patient, and wherein the analyzing comprises identifying the relevant information based at least in part on medical history data for the patient.

52. The apparatus of claim 30, wherein the generating is performed using at least one model trained on past sterile procedure reports.

53. The apparatus of claim 52, wherein the at least one model is specific to one of the one or more clinical personnel who authorizes the text report.

54. The apparatus of claim 30, wherein the generating comprises copying text from at least one past medical report that also included the relevant information.

55. The apparatus of claim 30, wherein the method further comprises allowing a human user to make edits to the text report.

56. The apparatus of claim 55, wherein the method further comprises updating at least one model used in the generating based on the human user's edits to the text report.

57. The apparatus of claim 55, wherein the method further comprises prompting the human user to add information to the text report to comply with one or more report content standards.

58. The apparatus of claim 30, wherein the sterile procedure is performed on a patient, and wherein the method further comprises including at least part of the relevant information in a discrete structured data repository for the patient.

59. At least one non-transitory computer-readable storage medium encoded with computer-executable instructions that, when executed, perform a method comprising:
transcribing audio data comprising audio of one or more clinical personnel speaking while performing a sterile procedure, the audio data comprising audio of a first clinician speaking to one or more other clinical personnel while performing the sterile procedure, wherein transcribing the audio data comprises performing automatic speech recognition (ASR) on the audio data using a speech recognition model trained to recognize speech of the first clinician;
analyzing the transcribed audio data, including the transcribed audio of the first clinician speaking to the one or more other clinical personnel while performing the sterile procedure, to identify relevant information for documenting the sterile procedure, the analyzing comprising:
identifying within the transcribed audio data a statement made by the first clinician to the other clinical personnel while performing the sterile procedure,
automatically determining whether information in the statement is relevant for documenting the sterile procedure,
if it is determined that the information in the statement is relevant for documenting the sterile procedure, automatically designating the relevant information for inclusion in documentation of the sterile procedure, and
if it is determined that the information in the statement is not relevant for documenting the sterile procedure, disregarding the statement in documenting the sterile procedure; and
automatically generating a text report including the designated relevant information documenting the sterile procedure;
wherein determining that the information in the statement is relevant for documenting the sterile procedure comprises detecting in the statement a present-tense narration by the first clinician stating to the other clinical personnel that the first clinician is currently performing a particular step of the sterile procedure;
wherein automatically generating the text report comprises automatically transforming the present-tense narration into a non-present-tense text portion in the report, stating that the particular step of the sterile procedure was performed.

60. The at least one computer-readable storage medium of claim 59, wherein the statement comprises the first clinician orally identifying an instrument being used in performing the sterile procedure, wherein the analyzing comprises automatically determining from the transcribed audio data a step of the sterile procedure performed using the instrument, and wherein generating the text report comprises automatically generating text stating that the step of the sterile procedure was performed using the instrument.

61. The at least one computer-readable storage medium of claim 59, wherein the statement comprises the first clinician orally identifying an action being performed during the sterile procedure, wherein the analyzing comprises automatically determining whether the action is part of a step of the sterile procedure that is relevant for documenting the sterile procedure, and wherein generating the text report comprises, in response to determining that the action is part of a step of the sterile procedure that is relevant for documenting the sterile procedure, automatically generating text stating that the step was performed.

62. The at least one computer-readable storage medium of claim 59, wherein the statement comprises the first clinician orally identifying an event occurring during the sterile procedure, wherein the analyzing comprises automatically determining whether the event indicates that a patient suffered a complication of the sterile procedure, and wherein generating the text report comprises, in response to determining that the event indicates that the patient suffered a complication of the sterile procedure, automatically generating text stating that the event occurred as a complication.

63. The at least one computer-readable storage medium of claim 59, wherein the sterile procedure is performed on a patient, wherein the statement comprises the first clinician orally identifying one or more observations of a condition of the patient during the sterile procedure, wherein the analyzing comprises automatically determining whether the observed condition of the patient indicates that the patient suffered a complication of the sterile procedure, and wherein generating the text report comprises, in response to determining that the observed condition indicates that the patient suffered a complication of the sterile procedure, automatically generating text stating that the condition was observed as a complication.

64. The at least one computer-readable storage medium of claim 59, wherein the sterile procedure is performed on a patient, wherein the statement comprises the first clinician orally identifying one or more substances administered to the patient in connection with the sterile procedure, and wherein generating the text report comprises automatically generating text stating that the one or more substances were administered.

65. The at least one computer-readable storage medium of claim 59, wherein the method further comprises recording the audio data through one or more microphones installed in a room in which the sterile procedure is performed.

66. The at least one computer-readable storage medium of claim 59, wherein the method further comprises recording the audio data through one or more microphones worn by the one or more clinical personnel.

67. The at least one computer-readable storage medium of claim 59, wherein the ASR is performed using different speaker-specific models for audio produced by different speakers from among the one or more clinical personnel.

68. The at least one computer-readable storage medium of claim 59, wherein the ASR is performed using a different language model for the sterile procedure than for a different sterile procedure.

69. The at least one computer-readable storage medium of claim 59, wherein the sterile procedure is a first type of sterile procedure, and wherein the ASR is performed using a language model trained to be specific to the first type of sterile procedure.

70. The at least one computer-readable storage medium of claim 59, wherein the method further comprises allowing a human to verify accuracy of the ASR transcription before performing the analyzing.

71. The at least one computer-readable storage medium of claim 59, wherein the analyzing is performed using at least one model trained on past sterile procedure reports, past audio transcriptions and/or medical literature.

72. The at least one computer-readable storage medium of claim 59, wherein the analyzing is performed using a different model for the sterile procedure than for a different sterile procedure.

73. The at least one computer-readable storage medium of claim 59, wherein the sterile procedure is a first type of sterile procedure, and wherein the analyzing is performed using a model trained to be specific to the first type of sterile procedure.

74. The at least one computer-readable storage medium of claim 59, wherein the ASR is performed using different language models for different stages of the sterile procedure.

75. The at least one computer-readable storage medium of claim 59, wherein the analyzing comprises identifying the relevant information based at least in part on rules regarding information to be documented for an institution responsible for the sterile procedure.

76. The at least one computer-readable storage medium of claim 59, wherein the analyzing comprises identifying the relevant information based at least in part on identifying which portions of the audio were spoken by which of the one or more clinical personnel.

77. The at least one computer-readable storage medium of claim 59, wherein the analyzing comprises determining, from the audio data, timing information for at least one step performed during the sterile procedure, and including the timing information in the relevant information.

78. The at least one computer-readable storage medium of claim 59, wherein the analyzing comprises identifying the relevant information based at least in part on patient monitoring data recorded using monitoring equipment during the sterile procedure.

79. The at least one computer-readable storage medium of claim 78, wherein the method further comprises synchronizing timing information from the patient monitoring data with timing information from the audio data.

80. The at least one computer-readable storage medium of claim 59, wherein the sterile procedure is performed on a patient, and wherein the analyzing comprises identifying the relevant information based at least in part on medical history data for the patient.

81. The at least one computer-readable storage medium of claim 59, wherein the generating is performed using at least one model trained on past sterile procedure reports.

82. The at least one computer-readable storage medium of claim 81, wherein the at least one model is specific to one of the one or more clinical personnel who authorizes the text report.

83. The at least one computer-readable storage medium of claim 59, wherein the generating comprises copying text from at least one past medical report that also included the relevant information.

84. The at least one computer-readable storage medium of claim 59, wherein the method further comprises allowing a human user to make edits to the text report.

85. The at least one computer-readable storage medium of claim 84, wherein the method further comprises updating at least one model used in the generating based on the human user's edits to the text report.

86. The at least one computer-readable storage medium of claim 84, wherein the method further comprises prompting the human user to add information to the text report to comply with one or more report content standards.

87. The at least one computer-readable storage medium of claim 59, wherein the sterile procedure is performed on a patient, and wherein the method further comprises including at least part of the relevant information in a discrete structured data repository for the patient.

* * * * *